US008318909B2

(12) United States Patent
Schuh et al.

(10) Patent No.: US 8,318,909 B2
(45) Date of Patent: Nov. 27, 2012

(54) ANTIBODIES FOR DIAGNOSIS AND TREATMENT OF BLOOD PLATELET ALLOIMMUNE DISORDERS

(76) Inventors: Andre Schuh, Toronto (CA); Willem Ouwehand, London (GB)

( * ) Notice: Subject to any disclaimer, the term of this patent is extended or adjusted under 35 U.S.C. 154(b) by 0 days.

(21) Appl. No.: 12/819,748

(22) Filed: Jun. 21, 2010

(65) Prior Publication Data
US 2011/0021759 A1  Jan. 27, 2011

Related U.S. Application Data

(62) Division of application No. 10/471,327, filed as application No. PCT/CA02/00291 on Mar. 2, 2002, now Pat. No. 7,741,029.

(60) Provisional application No. 60/273,941, filed on Mar. 7, 2001.

(51) Int. Cl.
*C07K 16/00* (2006.01)

(52) U.S. Cl. ............... 530/387.9; 530/387.1; 530/388.7; 530/391.1; 530/806; 435/7.1; 435/7.92; 435/7.94

(58) Field of Classification Search .................. None
See application file for complete search history.

(56) References Cited

U.S. PATENT DOCUMENTS
5,474,796 A  12/1995 Brennan

FOREIGN PATENT DOCUMENTS
| WO | WO 91 03557 | 3/1991 |
| WO | WO 00 29448 | 5/2000 |
| WO | WO 02 070696 | 9/2002 |
| WO | WO 02 085942 | 10/2002 |

OTHER PUBLICATIONS

Janeway et al., Immunobiology, 3rd edition, Garland Publishing Inc., 1997, pp. 2:8-2:11.*
Beezhold et al., Clin Exp Immunol. Apr. 1997;108(1):114-21.*
Strynadka et al., J Virol. Sep. 1988; 62(9): 3474-3483.*
van Kampen et al., Allergy. Feb. 2001;56(2):118-25.*
H.M. DeLisser. "Epitope Mapping." Methods in Molecular Biology, vol. 96: Adhesion Protein Protocols, 1999, pp. 11-20.
C. Meier and J.W. Engels. "Peptide Nucleic Acids (PNAs)—Unusual Properties of Nonionic Oligonucleotide Analogues." Angew. Chem. Int. Ed. Engl. 1992, vol. 31, No. 8, pp. 1008-1010.
U. Englisch and D.H. Gauss. "Chemically Modified Oligonucleotides as Probes and Inhibitors." Angew. Chem. Int. Ed. Engl., vol. 30, No. 6, Jun. 1991, pp. 613-629.
F. Felici et al. "Peptide and protein display on the surface of filamentous bacteriophage." Biotechnology Annual Review, vol. 1, 1995, pp. 149-183.
W. Gish and D.J. States. "Identification of protein coding regions by database similarity search." Nature Genetics, vol. 3, Mar. 1993, pp. 266-272.
E.S. Kawasaki. "Amplification of RNA." PCR Protocols: A guide to Methods and Applications, Academic Press Inc., 1990, pp. 21-27.
T.L. Madden et al. "Network BLAST Server Applications." Methods in Enzymology, vol. 266 (1996) pp. 131-141.
B.A. Morgan and J.A. Gainor. "Approaches to the Discovery of Non-Peptide Ligands for Peptide Receptors and Peptidases." Annual Reports in Medicinal Chemistry, Section VI—Topics in Chemistry and Drug Design, Chapter 26, 1989, pp. 243-252.
U. Reineke et al. "Antigen Sequence- and Library-Based Mapping of Linear and Discontinuous Protein-Protein-Interaction Sites by Spot Synthesis." Current Topics in Microbiology and Immunology, 243 (1999), pp. 23-36.
A.C. Schuh et al. "Cell Surface Antigen CD109 Is a Novel Member of the a2 Macroglobulin/C3, C4, C5 Family of Thioester Containing Proteins." Blood 98 (11):50b (2001).
R. Steen and T. Egeland. "CD34 Molecule Epitope Distribution on Cells of Haematopoietic Origin." Leukemia and Lymphoma, 1998, vol. 30, pp. 23-30.
D.R. Sutherland and E.L. Yeo. "CDw109 Cluster report." Leukocyte Typing V (Schlossman S. et al eds.), Oxford University Press, Oxford, pp. 1767-1769, 1995.
B. Westerlund-Wikstorm. "Peptide display on bacterial flagella: Principles and applications." Int. J. Med. Microbiol., 290, pp. 223-230 (2000).
Database EMBL Online, Feb. 2, 2001. "Hydrophobic domain protein isolated from HT-1080 cells." retrieved from EBI Database accession No. AAB12127.
J.F. Yu et al. "Comparison of the expression of CD109 and CD135 on CD34+ cells in human marrow, cord blood, and peripheral blood." Blood, vol. 94, No. 10, Suppl. 1, Part 2, Nov. 1999, p. 136b.
Database EMBL 'Online, Feb 2, 2001. "Hydrophobic domain protein cDNA HP02837 isolated from HT-1080 cells." Retrieved from EBI, Database accession No. AAA62010.
S.F. Altschul et al. "Basic Local Alignment Search Tool." J. Mol. Biol. (1990) 215, pp. 403-410.
S.F. Altschul et al. "Gapped BLAST and PSI-BLAST: A new generation of protein database search programs." Nucleic Acids Research, 1997, vol. 25, No. 17, pp. 3389-3402.
D. R. Burton. "Commentary Phage Display." Immunotechnology 1, (1995), pp. 87-94.
R. Cortese et al. "Selection of biologically active peptides by phage display of random peptide libraries." Current Opinion in Biotechnology, 1996, vol. 7, pp. 616-621.
J. M. Gershoni et al. "Combinatorial libraries, epitope structure and the prediction of protein conformation." Immunology Today, Mar. 1997, vol. 18, Issue 3, pp. 108-110.

(Continued)

*Primary Examiner* — Michael Szperka
(74) *Attorney, Agent, or Firm* — Ballard Spahr LLP

(57) ABSTRACT

Based on the discovery of the nucleotide and amino acid differences which distinguish the Gov$^a$ and Gov$^b$ allelic forms of the membrane glycoprotein CD109, and which comprise the biallelic Gov platelet alloantigen system, compositions and methods are provided for determining the Gov genotype and phenotype of individuals. Also provided, on the basis of this discovery, are compositions and methods for treating disorders associated with Gov alloantigen incompatibility, such as the bleeding disorders post-transfusion purpura, post-transfusion platelet refractoriness, and neonatal alloimmune thrombocytopenia. The two allelic forms of CD109 differ by a single amino acid. The Gov$^a$ allelic form has Tyr at amino acid position 703 in the CD109 sequence. The Gov$^b$ allelic form has Ser at the same position. This amino acid difference is due to a single change, from A for the Gov$^a$ allele to C for the Gov$^b$ allele, in the CD109 gene.

12 Claims, No Drawings

OTHER PUBLICATIONS

J. Goodchild. "Conjugates of Oligonucleotides and Modified Oligonucleotides: A Review of Their Synthesis and Properties." Bioconjugate Chemistry, May/Jun. 1990, vol. 1, No. 3, pp. 165-187.

E. Lesnik et al. "Oligodeoxynucleotides Containing 2'-O-Modified Adenosine: Synthesis and Effects on Stability of DNA:RNA Duplexes." Biochemistry, 1993, vol. 32, No. 30, pp. 7832-7838.

J. Tseng-Law et al. "Identification of a peptide directed against the anti-CD34 antibody, 9C5, by phage display and its use in hematopoietic stem cell selection." Experimental Hematology, 1999, vol. 27, 936-945.

J. Van de Water et al. "Detection of Molecular Determinants and Epitope Mapping Using Maldi-TOF Mass Spectrometry." Clinical Immunology and Immunopathology, vol. 85, No. 3, Dec. 1997, pp. 229-235.

M. H. V. Van Regenmortel et al. "Measurement of antigen-antibody interactions with biosensors." Journal of Molecular Recognition, 1998, vol. 11, pp. 163-167.

J. Zhang and T. L. Madden. "PowerBLAST: A New Network BLAST Application for Interactive or Automated Sequence Analysis and Annotation." Genome Research, 1997, pp. 649-656.

Scuciu-Foca N., Reed E., Rubensein P., MacKanzy W., Ng AK, King DW. "A late-differentiation antigen assocated with the helper inducer function of human T cells." Nature. 1985; 318, 465-467.

Brashem-Stein C., Nugent D., Bernstein ID. "Characterization of an antigen expressed on activated human T cells and platelets." J. Immunol. 1988; 140:2330-2333.

Haregewoin A., Solomon K., Horn RC, et al. "Cellular expression of a GPI-linked T cell activation protein." Cell Immunol. 1994; 156:357-333.

Solomon KR, Mallory MA, Finberg RW, "Determination of the non-ionic detergent insolubility and phosphoprotein associations of glycosylphosphatidylinosito-anchored proteins expressed on T cells." Biochem J. 1998;334:325-333.

Totty NF, Waterfield MD, Hsuan JJ. "Accelerated high-sensitivity microsequencing of proteins and peptides using a miniature reaction cartridge." Protein Sci. 1992; 1:1215-1224.

Murray LJ, Bruno E, Uchida N, et al. "CD109 is expressed on a subpopulation of CD34+ cells enriched in hematopoietic stem and progenitor cells." Exp Hematol 1999;27:1282-1294.

J.O. Bordin et al. "Maternal Immunization to Gov system alloantigens on human platelets." Transfusion, Vo. 37, No. 8, Aug. 1997, pp. 823-828.

R.W.A.M. Kujipers et al. "NH(2)-Terminal Globular Domain of Human Platelet Glycoprotein Ibα Has a Methionine(145)/Threonine(145) Amino Acid Polymorphism, Which is Associated with the HPA-2(Ko) Alloantigens." J. Clin. Invest., vol. 89, Feb. 1992, pp. 381-384.

T. Nakatani et al. "Functional Expression of Human Monoclonal Antibody Genes Directed Against Pseudomonal Exotoxin A in Mouse Myeloma Cells." Bio/Technology, vol. 7, Aug. 1989, pp. 805-810.

P.J. Newman et al. "Enzymatic Amplification of Platelet-specific Messenger RNA Using the Polymerase Chain Reaction." J. Clin. Invest. vol. 82, Aug. 1998, pp. 739-743.

P.J. Newman et al. "The Human Platelet Alloantigens, PI (A1) and PL (A2), Are Associated with a Laucine (33)/Proline(33) Amino Acid Polymorphism in Membrame Glycoprotein IIIa, and Are Distinguishable by DNA Typing." J. Clin.Invest., vol. 83, May 1989, pp. 1778-1781.

P.E. Nielsen et. al. "Peptide nucleic acids (PNAs); Potential antisense and anti-gene agents." Anti-Cancer Drug Design (1993), 8, pp. 53-63.

W. Ouwehand & C. Navarrete. "The molecular basis of blood cell alloantigens." Molecular Haematology, Provan and Gribben (Eds), Blackwell Science (2000), Chapter 14, pp. 182-197.

D.R. Sutherland et al. "Identification of a Cell-Surface Antigen Associated With Activated T. Lymphoblasts and Activated Platelets." Blood, vol. 77, No. 1 Jan. 1, 1991, pp. 84-93.

R. Wang et al. "An Amino Acid Polymorphism within the RGD Binding Domain of Platelet Membrane Glycoprotein IIIa is Responsible for the Formation of the Pen(a)/Pen(b) Alloantigen System." J. Clin. Invest. vol. 90, Nov. 1992, pp. 2038-2043.

E.S. Ward et al."Binding activities of a repertiore of single immunoglobulin variable domains secreted from *Escherichia coli*." Nature, vol. 341, Oct. 12, 1989, pp. 544-546.

J.W. Smith et al. "Investigation of human platelet alloantigens and glycoproteins using non-radioactive immunoprecipitation." Journal of Immunological Methods, vol. 158, No. 1, 1993, pp. 77-85.

J.W. Smith et al. "Characterization and localization of the Gov(ab) alloantigens to the Glycosylphosphatidylinositol-Anchored Protein CDw109 on Human Platelets." Blood, vol. 86, No. 7, Oct. 1995, pp. 2807-2814.

J.E. Berry et al. "Detection of Gov. system antibodies by MAIPA reveals an immunogencity similar to the HPA-5 alloantigens." British Journal of Haematology, vol. 110, No. 3, Sep. 2000, pp. 735-742.

J.G. Kelton et al. "Gov(ab) Alloantigen System on Human Platelets." Blood vol. 75, No. 11, Jun. 1990, pp. 2172-2176.

S. Lyman et al. "Polymorphism of Human Platelet Membrane Glycoprotein IIb Associated With the Bak(a)/Bak(b) Alloatigen System." Blood, vol. 75, No. 12, Jun. 1990, pp. 2343-2348.

J.G. Kelton et al. "ABH antigens on human platelets: Expression on the Glycosylphosphatidylinositol-Anchored Protein CD 109." Journal of Laboratory and Clinical Medicine, vol. 132, No. 2, Aug. 1998, pp. 142-148.

A.C. Schuh et al. "A tyrosine703serine polmorphism of CD109 defines the Gov Platelet allontigens." Blood, vol. 99, No. 5, Mar. 2002, pp. 1692-1698.

Mohr, W.D. et al., "Mixing in Laminar-Flow Systems," 1957, ACS, Industrial and Engineering Chemistry, vol. 49, No. 11.

Notice of Allowance and Fees Due dated Nov. 17, 2009 from U.S. Appl. No. 10/471,345.

Response to Office Action dated Aug. 11, 2009 from U.S. Appl. No. 10/471,345.

Office Action dated Feb. 11, 2009 from U.S. Appl. No. 10/471,345.

Request for Continued Examination and Amendments dated Dec. 23, 2008 from U.S. Appl. No. 10/471,345.

Final Rejection dated Jun. 20, 2008 from U.S. Appl. No. 10/471,345.

Response to Office Action dated Mar. 5, 2008 from U.S. Appl. No. 10/471,345.

Advisory Action Before Filing Appeal dated Sep. 20, 2007 from U.S. Appl. No. 10/471,345.

Office Action dated Sep. 5, 2007 from U.S. Appl. No. 10/471,345.

Response to Restriction Requirement dated Jul. 10, 2007 from U.S. Appl. No. 10/471,345.

Restriction Requirement dated Jan. 11, 2007 from U.S. Appl. No. 10/471,345.

Preliminary Amendment dated Sep. 8, 2003 from U.S. Appl. No. 10/471,345.

* cited by examiner

SEQUENCE LISTING

```
<160> NUMBER OF SEQ ID NOS: 30

<210> SEQ ID NO 1
<211> LENGTH: 4335
<212> TYPE: DNA
<213> ORGANISM: Homo sapiens
<220> FEATURE:
<221> NAME/KEY: CDS
<222> LOCATION: (1)..(4335)

<400> SEQUENCE: 1 atg cag ggc cca ccg ctc ctg acc gcc gcc cac ctc ctc tgc gtg tgc        48
Met Gln Gly Pro Pro Leu Leu Thr Ala Ala His Leu Leu Cys Val Cys
1               5                   10                  15 acc gcc gcg ctg gcc gtg gct ccc ggg cct cgg ttt ctg gtg aca gcc        96
Thr Ala Ala Leu Ala Val Ala Pro Gly Pro Arg Phe Leu Val Thr Ala
                20                  25                  30 cca ggg atc atc agg ccc gga gga aat gtg act att ggg gtg gag ctt       144
Pro Gly Ile Ile Arg Pro Gly Gly Asn Val Thr Ile Gly Val Glu Leu
            35                  40                  45 ctg gaa cac tgc cct tca cag gtg act gtg aag gcg gag ctg ctc aag       192
Leu Glu His Cys Pro Ser Gln Val Thr Val Lys Ala Glu Leu Leu Lys
        50                  55                  60 aca gca tca aac ctc act gtc tct gtc ctg gaa gca gaa gga gtc ttt       240
Thr Ala Ser Asn Leu Thr Val Ser Val Leu Glu Ala Glu Gly Val Phe
65                  70                  75                  80 gaa aaa ggc tct ttt aag aca ctt act ctt cca tca cta cct ctg aac       288
Glu Lys Gly Ser Phe Lys Thr Leu Thr Leu Pro Ser Leu Pro Leu Asn
                85                  90                  95 agt gca gat gag att tat gag cta cgt gta acc gga cgt acc cag gat       336
Ser Ala Asp Glu Ile Tyr Glu Leu Arg Val Thr Gly Arg Thr Gln Asp
            100                 105                 110 gag att tta ttc tct aat agt acc cgc tta tca ttt gag acc aag aga       384
Glu Ile Leu Phe Ser Asn Ser Thr Arg Leu Ser Phe Glu Thr Lys Arg
        115                 120                 125 ata tct gtc ttc att caa aca gac aag gcc tta tac aag cca aag caa       432
Ile Ser Val Phe Ile Gln Thr Asp Lys Ala Leu Tyr Lys Pro Lys Gln
    130                 135                 140 gaa gtg aag ttt cgc att gtt aca ctc ttc tca gat ttt aag cct tac       480
Glu Val Lys Phe Arg Ile Val Thr Leu Phe Ser Asp Phe Lys Pro Tyr
145                 150                 155                 160
```

| | | |
|---|---|---|
| aaa acc tct tta aac att ctc att aag gac ccc aaa tca aat ttg atc<br>Lys Thr Ser Leu Asn Ile Leu Ile Lys Asp Pro Lys Ser Asn Leu Ile<br>165 170 175 | | 528 |
| caa cag tgg ttg tca caa caa agt gat ctt gga gtc att tcc aaa act<br>Gln Gln Trp Leu Ser Gln Gln Ser Asp Leu Gly Val Ile Ser Lys Thr<br>180 185 190 | | 576 |
| ttt cag cta tct tcc cat cca ata ctt ggt gac tgg tct att caa gtt<br>Phe Gln Leu Ser Ser His Pro Ile Leu Gly Asp Trp Ser Ile Gln Val<br>195 200 205 | | 624 |
| caa gtg aat gac cag aca tat tat caa tca ttt cag gtt tca gaa tat<br>Gln Val Asn Asp Gln Thr Tyr Tyr Gln Ser Phe Gln Val Ser Glu Tyr<br>210 215 220 | | 672 |
| gta tta cca aaa ttt gaa gtg act ttg cag aca cca tta tat tgt tct<br>Val Leu Pro Lys Phe Glu Val Thr Leu Gln Thr Pro Leu Tyr Cys Ser<br>225 230 235 240 | | 720 |
| atg aat tct aag cat tta aat ggt acc atc acg gca aag tat aca tat<br>Met Asn Ser Lys His Leu Asn Gly Thr Ile Thr Ala Lys Tyr Thr Tyr<br>245 250 255 | | 768 |
| ggg aag cca gtg aaa gga gac gta acg ctt aca ttt tta cct tta tcc<br>Gly Lys Pro Val Lys Gly Asp Val Thr Leu Thr Phe Leu Pro Leu Ser<br>260 265 270 | | 816 |
| ttt tgg gga aag aag aaa aat att aca aaa aca ttt aag ata aat gga<br>Phe Trp Gly Lys Lys Lys Asn Ile Thr Lys Thr Phe Lys Ile Asn Gly<br>275 280 285 | | 864 |
| tct gca aac ttc tct ttt aat gat gaa gag atg aaa aat gta atg gat<br>Ser Ala Asn Phe Ser Phe Asn Asp Glu Glu Met Lys Asn Val Met Asp<br>290 295 300 | | 912 |
| tct tca aat gga ctt tct gaa tac ctg gat cta tct tcc cct gga cca<br>Ser Ser Asn Gly Leu Ser Glu Tyr Leu Asp Leu Ser Ser Pro Gly Pro<br>305 310 315 320 | | 960 |
| gta gaa att tta acc aca gtg aca gaa tca gtt aca ggt att tca aga<br>Val Glu Ile Leu Thr Thr Val Thr Glu Ser Val Thr Gly Ile Ser Arg<br>325 330 335 | | 1008 |
| aat gta agc act aat gtg ttc ttc aag caa cat gat tac atc att gag<br>Asn Val Ser Thr Asn Val Phe Phe Lys Gln His Asp Tyr Ile Ile Glu<br>340 345 350 | | 1056 |
| ttt ttt gat tat act act gtc ttg aag cca tct ctc aac ttc aca gcc<br>Phe Phe Asp Tyr Thr Thr Val Leu Lys Pro Ser Leu Asn Phe Thr Ala<br>355 360 365 | | 1104 |
| act gtg aag gta act cgt gct gat ggc aac caa ctg act ctt gaa gaa<br>Thr Val Lys Val Thr Arg Ala Asp Gly Asn Gln Leu Thr Leu Glu Glu<br>370 375 380 | | 1152 |
| aga aga aat aat gta gtc ata aca gtg aca cag aga aac tat act gag<br>Arg Arg Asn Asn Val Val Ile Thr Val Thr Gln Arg Asn Tyr Thr Glu<br>385 390 395 400 | | 1200 |
| tac tgg agc gga tct aac agt gga aat cag aaa atg gaa gct gtt cag<br>Tyr Trp Ser Gly Ser Asn Ser Gly Asn Gln Lys Met Glu Ala Val Gln<br>405 410 415 | | 1248 |
| aaa ata aat tat act gtc ccc caa agt gga act ttt aag att gaa ttc<br>Lys Ile Asn Tyr Thr Val Pro Gln Ser Gly Thr Phe Lys Ile Glu Phe<br>420 425 430 | | 1296 |
| cca atc ctg gag gat tcc agt gag cta cag ttg aag gcc tat ttc ctt<br>Pro Ile Leu Glu Asp Ser Ser Glu Leu Gln Leu Lys Ala Tyr Phe Leu<br>435 440 445 | | 1344 |
| ggt agt aaa agt agc atg gca gtt cat agt ctg ttt aag tct cct agt<br>Gly Ser Lys Ser Ser Met Ala Val His Ser Leu Phe Lys Ser Pro Ser<br>450 455 460 | | 1392 |
| aag aca tac atc caa cta aaa aca aga gat gaa aat ata aag gtg gga<br>Lys Thr Tyr Ile Gln Leu Lys Thr Arg Asp Glu Asn Ile Lys Val Gly<br>465 470 475 480 | | 1440 |

```
                                              -continued tcg cct ttt gag ttg gtg gtt agt ggc aac aaa cga ttg aag gag tta      1488
Ser Pro Phe Glu Leu Val Val Ser Gly Asn Lys Arg Leu Lys Glu Leu
                485                 490                 495 agc tat atg gta gta tcc agg gga cag ttg gtg gct gta gga aaa caa      1536
Ser Tyr Met Val Val Ser Arg Gly Gln Leu Val Ala Val Gly Lys Gln
        500                 505                 510 aat tca aca atg ttc tct tta aca cca gaa aat tct tgg act cca aaa      1584
Asn Ser Thr Met Phe Ser Leu Thr Pro Glu Asn Ser Trp Thr Pro Lys
    515                 520                 525 gcc tgt gta att gtg tat tat att gaa gat gat ggg gaa att ata agt      1632
Ala Cys Val Ile Val Tyr Tyr Ile Glu Asp Asp Gly Glu Ile Ile Ser
530                 535                 540 gat gtt cta aaa att cct gtt cag ctt gtt ttt aaa aat aag ata aag      1680
Asp Val Leu Lys Ile Pro Val Gln Leu Val Phe Lys Asn Lys Ile Lys
545                 550                 555                 560 cta tat tgg agt aaa gtg aaa gct gaa cca tct gag aaa gtc tct ctt      1728
Leu Tyr Trp Ser Lys Val Lys Ala Glu Pro Ser Glu Lys Val Ser Leu
                565                 570                 575 agg atc tct gtg aca cag cct gac tcc ata gtt ggg att gta gct gtt      1776
Arg Ile Ser Val Thr Gln Pro Asp Ser Ile Val Gly Ile Val Ala Val
            580                 585                 590 gac aaa agt gtg aat ctg atg aat gcc tct aat gat att aca atg gaa      1824
Asp Lys Ser Val Asn Leu Met Asn Ala Ser Asn Asp Ile Thr Met Glu
        595                 600                 605 aat gtg gtc cat gag ttg gaa ctt tat aac aca gga tat tat tta ggc      1872
Asn Val Val His Glu Leu Glu Leu Tyr Asn Thr Gly Tyr Tyr Leu Gly
    610                 615                 620 atg ttc atg aat tct ttt gca gtc ttt cag gaa tgt gga ctc tgg gta      1920
Met Phe Met Asn Ser Phe Ala Val Phe Gln Glu Cys Gly Leu Trp Val
625                 630                 635                 640 ttg aca gat gca aac ctc acg aag gat tat att gat ggt gtt tat gac      1968
Leu Thr Asp Ala Asn Leu Thr Lys Asp Tyr Ile Asp Gly Val Tyr Asp
                645                 650                 655 aat gca gaa tat gct gag agg ttt atg gag gaa aat gaa gga cat att      2016
Asn Ala Glu Tyr Ala Glu Arg Phe Met Glu Glu Asn Glu Gly His Ile
            660                 665                 670 gta gat att cat gac ttt tct ttg ggt agc agt cca cat gtc cga aag      2064
Val Asp Ile His Asp Phe Ser Leu Gly Ser Ser Pro His Val Arg Lys
        675                 680                 685 cat ttt cca gag act tgg att tgg cta gac acc aac atg ggt tac agg      2112
His Phe Pro Glu Thr Trp Ile Trp Leu Asp Thr Asn Met Gly Tyr Arg
    690                 695                 700 att tac caa gaa ttt gaa gta act gta cct gat tct atc act tct tgg      2160
Ile Tyr Gln Glu Phe Glu Val Thr Val Pro Asp Ser Ile Thr Ser Trp
705                 710                 715                 720 gtg gct act ggt ttt gtg atc tct gag gac ctg ggt ctt gga cta aca      2208
Val Ala Thr Gly Phe Val Ile Ser Glu Asp Leu Gly Leu Gly Leu Thr
                725                 730                 735 act act cca gtg gag ctc caa gcc ttc caa cca ttt ttc att ttt ttg      2256
Thr Thr Pro Val Glu Leu Gln Ala Phe Gln Pro Phe Phe Ile Phe Leu
            740                 745                 750 aat ctt ccc tac tct gtt atc aga ggt gaa gaa ttt gct ttg gaa ata      2304
Asn Leu Pro Tyr Ser Val Ile Arg Gly Glu Glu Phe Ala Leu Glu Ile
        755                 760                 765 act ata ttc aat tat ttg aaa gat gcc act gag gtt aag gta atc att      2352
Thr Ile Phe Asn Tyr Leu Lys Asp Ala Thr Glu Val Lys Val Ile Ile
    770                 775                 780 gag aaa agt gac aaa ttt gat att cta atg act tca aat gaa ata aat      2400
Glu Lys Ser Asp Lys Phe Asp Ile Leu Met Thr Ser Asn Glu Ile Asn
785                 790                 795                 800
```

```
gcc aca ggc cac cag cag acc ctt ctg gtt ccc agt gag gat ggg gca      2448
Ala Thr Gly His Gln Gln Thr Leu Leu Val Pro Ser Glu Asp Gly Ala
                805                 810                 815 act gtt ctt ttt ccc atc agg cca aca cat ctg gga gaa att cct atc      2496
Thr Val Leu Phe Pro Ile Arg Pro Thr His Leu Gly Glu Ile Pro Ile
            820                 825                 830 aca gtc aca gct ctt tca ccc act gct tct gat gct gtc acc cag atg      2544
Thr Val Thr Ala Leu Ser Pro Thr Ala Ser Asp Ala Val Thr Gln Met
        835                 840                 845 att tta gta aag gct gaa gga ata gaa aaa tca tat tca caa tcc atc      2592
Ile Leu Val Lys Ala Glu Gly Ile Glu Lys Ser Tyr Ser Gln Ser Ile
    850                 855                 860 tta tta gac ttg act gac aat agg cta cag agt acc ctg aaa act ttg      2640
Leu Leu Asp Leu Thr Asp Asn Arg Leu Gln Ser Thr Leu Lys Thr Leu
865                 870                 875                 880 agt ttc tca ttt cct cct aat aca gtg act ggc agt gaa aga gtt cag      2688
Ser Phe Ser Phe Pro Pro Asn Thr Val Thr Gly Ser Glu Arg Val Gln
                885                 890                 895 atc act gca att gga gat gtt ctt ggt cct tcc atc aat ggc tta gcc      2736
Ile Thr Ala Ile Gly Asp Val Leu Gly Pro Ser Ile Asn Gly Leu Ala
            900                 905                 910 tca ttg att cgg atg cct tat ggc tgt ggt gaa cag aac atg ata aat      2784
Ser Leu Ile Arg Met Pro Tyr Gly Cys Gly Glu Gln Asn Met Ile Asn
        915                 920                 925 ttt gct cca aat att tac att ttg gat tat ctg act aaa aag aaa caa      2832
Phe Ala Pro Asn Ile Tyr Ile Leu Asp Tyr Leu Thr Lys Lys Lys Gln
    930                 935                 940 ctg aca gat aat ttg aaa gaa aaa gct ctt tca ttt atg agg caa ggt      2880
Leu Thr Asp Asn Leu Lys Glu Lys Ala Leu Ser Phe Met Arg Gln Gly
945                 950                 955                 960 tac cag aga gaa ctt ctc tat cag agg gaa gat ggc tct ttc agt gct      2928
Tyr Gln Arg Glu Leu Leu Tyr Gln Arg Glu Asp Gly Ser Phe Ser Ala
                965                 970                 975 ttt ggg aat tat gac cct tct ggg agc act tgg ttg tca gct ttt gtt      2976
Phe Gly Asn Tyr Asp Pro Ser Gly Ser Thr Trp Leu Ser Ala Phe Val
            980                 985                 990 tta aga tgt ttc ctt gaa gcc gat cct tac ata gat att gat cag aat      3024
Leu Arg Cys Phe Leu Glu Ala Asp Pro Tyr Ile Asp Ile Asp Gln Asn
        995                 1000                1005 gtg tta cac aga aca tac act tgg ctt aaa gga cat cag aaa tcc           3069
Val Leu His Arg Thr Tyr Thr Trp Leu Lys Gly His Gln Lys Ser
    1010                1015                1020 aac ggt gaa ttt tgg gat cca gga aga gtg att cat agt gag ctt           3114
Asn Gly Glu Phe Trp Asp Pro Gly Arg Val Ile His Ser Glu Leu
1025                1030                1035 caa ggt ggc aat aaa agt cca gta aca ctt aca gcc tat att gta           3159
Gln Gly Gly Asn Lys Ser Pro Val Thr Leu Thr Ala Tyr Ile Val
    1040                1045                1050 act tct ctc ctg gga tat aga aag tat cag cct aac att gat gtg           3204
Thr Ser Leu Leu Gly Tyr Arg Lys Tyr Gln Pro Asn Ile Asp Val
1055                1060                1065 caa gag tct atc cat ttt ttg gag tct gaa ttc agt aga gga att           3249
Gln Glu Ser Ile His Phe Leu Glu Ser Glu Phe Ser Arg Gly Ile
    1070                1075                1080 tca gac aat tat act cta gcc ctt ata act tat gca ttg tca tca           3294
Ser Asp Asn Tyr Thr Leu Ala Leu Ile Thr Tyr Ala Leu Ser Ser
1085                1090                1095 gtg ggg agt cct aaa gcg aag gaa gct ttg aat atg ctg act tgg           3339
Val Gly Ser Pro Lys Ala Lys Glu Ala Leu Asn Met Leu Thr Trp
    1100                1105                1110
```

```
aga gca gaa caa gaa ggt ggc atg caa ttc tgg gtg tca tca gag    3384
Arg Ala Glu Gln Glu Gly Gly Met Gln Phe Trp Val Ser Ser Glu
1115                1120                1125 tcc aaa ctt tct gac tcc tgg cag cca cgc tcc ctg gat att gaa    3429
Ser Lys Leu Ser Asp Ser Trp Gln Pro Arg Ser Leu Asp Ile Glu
    1130                1135                1140 gtt gca gcc tat gca ctg ctc tca cac ttc tta caa ttt cag act    3474
Val Ala Ala Tyr Ala Leu Leu Ser His Phe Leu Gln Phe Gln Thr
1145                1150                1155 tct gag gga atc cca att atg agg tgg cta agc agg caa aga aat    3519
Ser Glu Gly Ile Pro Ile Met Arg Trp Leu Ser Arg Gln Arg Asn
    1160                1165                1170 agc ttg ggt ggt ttt gca tct act cag gat acc act gtg gct tta    3564
Ser Leu Gly Gly Phe Ala Ser Thr Gln Asp Thr Thr Val Ala Leu
1175                1180                1185 aag gct ctg tct gaa ttt gca gcc cta atg aat aca gaa agg aca    3609
Lys Ala Leu Ser Glu Phe Ala Ala Leu Met Asn Thr Glu Arg Thr
    1190                1195                1200 aat atc caa gtg acc gtg acg ggg cct agc tca cca agt cct gta    3654
Asn Ile Gln Val Thr Val Thr Gly Pro Ser Ser Pro Ser Pro Val
1205                1210                1215 aag ttt ctg att gac aca cac aac cgc tta ctc ctt cag aca gca    3699
Lys Phe Leu Ile Asp Thr His Asn Arg Leu Leu Leu Gln Thr Ala
    1220                1225                1230 gag ctt gct gtg gta cag cca atg gca gtt aat att tcc gca aat    3744
Glu Leu Ala Val Val Gln Pro Met Ala Val Asn Ile Ser Ala Asn
1235                1240                1245 ggt ttt gga ttt gct att tgt cag ctc aat gtt gta tat aat gtg    3789
Gly Phe Gly Phe Ala Ile Cys Gln Leu Asn Val Val Tyr Asn Val
    1250                1255                1260 aag gct tct ggg tct tct aga aga cga aga tct atc caa aat caa    3834
Lys Ala Ser Gly Ser Ser Arg Arg Arg Arg Ser Ile Gln Asn Gln
1265                1270                1275 gaa gcc ttt gat tta gat gtt gct gta aaa gaa aat aaa gat gat    3879
Glu Ala Phe Asp Leu Asp Val Ala Val Lys Glu Asn Lys Asp Asp
    1280                1285                1290 ctc aat cat gtg gat ttg aat gtg tgt aca agc ttt tcg ggc ccg    3924
Leu Asn His Val Asp Leu Asn Val Cys Thr Ser Phe Ser Gly Pro
1295                1300                1305 ggt agg agt ggc atg gct ctt atg gaa gtt aac cta tta agt ggc    3969
Gly Arg Ser Gly Met Ala Leu Met Glu Val Asn Leu Leu Ser Gly
    1310                1315                1320 ttt atg gtg cct tca gaa gca att tct ctg agc gag aca gtg aag    4014
Phe Met Val Pro Ser Glu Ala Ile Ser Leu Ser Glu Thr Val Lys
1325                1330                1335 aaa gtg gaa tat gat cat gga aaa ctc aac ctc tat tta gat tct    4059
Lys Val Glu Tyr Asp His Gly Lys Leu Asn Leu Tyr Leu Asp Ser
    1340                1345                1350 gta aat gaa acc cag ttt tgt gtt aat att cct gct gtg aga aac    4104
Val Asn Glu Thr Gln Phe Cys Val Asn Ile Pro Ala Val Arg Asn
1355                1360                1365 ttt aaa gtt tca aat acc caa gat gct tca gtg tcc ata gtg gat    4149
Phe Lys Val Ser Asn Thr Gln Asp Ala Ser Val Ser Ile Val Asp
    1370                1375                1380 tac tat gag cca agg aga cag gcg gtg aga agt tac aac tct gaa    4194
Tyr Tyr Glu Pro Arg Arg Gln Ala Val Arg Ser Tyr Asn Ser Glu
1385                1390                1395 gtg aag ctg tcc tcc tgt gac ctt tgc agt gat gtc cag ggc tgc    4239
Val Lys Leu Ser Ser Cys Asp Leu Cys Ser Asp Val Gln Gly Cys
    1400                1405                1410
```

-continued

| | | | | | | | | | | | | | | |
|---|---|---|---|---|---|---|---|---|---|---|---|---|---|---|
| cgt | cct | tgt | gag | gat | gga | gct | tca | ggc | tcc | cat | cat | cac | tct | tca | 4284 |
| Arg | Pro | Cys | Glu | Asp | Gly | Ala | Ser | Gly | Ser | His | His | His | Ser | Ser | |
| | 1415 | | | | 1420 | | | | 1425 | | | | | | |

| | | | | | | | | | | | | | | |
|---|---|---|---|---|---|---|---|---|---|---|---|---|---|---|
| gtc | att | ttt | att | ttc | tgt | ttc | aag | ctt | ctg | tac | ttt | atg | gaa | ctt | 4329 |
| Val | Ile | Phe | Ile | Phe | Cys | Phe | Lys | Leu | Leu | Tyr | Phe | Met | Glu | Leu | |
| 1430 | | | | | 1435 | | | | | 1440 | | | | | | tgg ctg  4335
Trp Leu
    1445

<210> SEQ ID NO 2
<211> LENGTH: 1445
<212> TYPE: PRT
<213> ORGANISM: Homo sapiens

<400> SEQUENCE: 2

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
    290                 295                 300

Ser Ser Asn Gly Leu Ser Glu Tyr Leu Asp Leu Ser Pro Gly Pro
305                 310                 315                 320

-continued

Val Glu Ile Leu Thr Thr Val Thr Glu Ser Val Thr Gly Ile Ser Arg
            325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
            355                 360                 365

Thr Val Lys Val Thr Arg Ala Asp Gly Asn Gln Leu Thr Leu Glu Glu
            370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
            405                 410                 415

Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
            435                 440                 445

Gly Ser Lys Ser Ser Met Ala Val His Ser Leu Phe Lys Ser Pro Ser
            450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
            485                 490                 495

Ser Tyr Met Val Val Ser Arg Gly Gln Leu Val Ala Val Gly Lys Gln
            500                 505                 510

Asn Ser Thr Met Phe Ser Leu Thr Pro Glu Asn Ser Trp Thr Pro Lys
            515                 520                 525

Ala Cys Val Ile Val Tyr Tyr Ile Glu Asp Asp Gly Glu Ile Ile Ser
            530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
            565                 570                 575

Arg Ile Ser Val Thr Gln Pro Asp Ser Ile Val Gly Ile Val Ala Val
            580                 585                 590

Asp Lys Ser Val Asn Leu Met Asn Ala Ser Asn Asp Ile Thr Met Glu
            595                 600                 605

Asn Val Val His Glu Leu Glu Leu Tyr Asn Thr Gly Tyr Tyr Leu Gly
            610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
            645                 650                 655

Asn Ala Glu Tyr Ala Glu Arg Phe Met Glu Glu Asn Glu Gly His Ile
            660                 665                 670

Val Asp Ile His Asp Phe Ser Leu Gly Ser Ser Pro His Val Arg Lys
            675                 680                 685

His Phe Pro Glu Thr Trp Ile Trp Leu Asp Thr Asn Met Gly Tyr Arg
            690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
            725                 730                 735

Thr Thr Pro Val Glu Leu Gln Ala Phe Gln Pro Phe Phe Ile Phe Leu

```
                   740                 745                 750
Asn Leu Pro Tyr Ser Val Ile Arg Gly Glu Glu Phe Ala Leu Glu Ile
            755                 760                 765
Thr Ile Phe Asn Tyr Leu Lys Asp Ala Thr Glu Val Lys Val Ile Ile
    770                 775                 780
Glu Lys Ser Asp Lys Phe Asp Ile Leu Met Thr Ser Asn Glu Ile Asn
785                 790                 795                 800
Ala Thr Gly His Gln Gln Thr Leu Leu Val Pro Ser Glu Asp Gly Ala
                805                 810                 815
Thr Val Leu Phe Pro Ile Arg Pro Thr His Leu Gly Glu Ile Pro Ile
            820                 825                 830
Thr Val Thr Ala Leu Ser Pro Thr Ala Ser Asp Ala Val Thr Gln Met
        835                 840                 845
Ile Leu Val Lys Ala Glu Gly Ile Glu Lys Ser Tyr Ser Gln Ser Ile
    850                 855                 860
Leu Leu Asp Leu Thr Asp Asn Arg Leu Gln Ser Thr Leu Lys Thr Leu
865                 870                 875                 880
Ser Phe Ser Phe Pro Pro Asn Thr Val Thr Gly Ser Glu Arg Val Gln
                885                 890                 895
Ile Thr Ala Ile Gly Asp Val Leu Gly Pro Ser Ile Asn Gly Leu Ala
            900                 905                 910
Ser Leu Ile Arg Met Pro Tyr Gly Cys Gly Glu Gln Asn Met Ile Asn
        915                 920                 925
Phe Ala Pro Asn Ile Tyr Ile Leu Asp Tyr Leu Thr Lys Lys Lys Gln
    930                 935                 940
Leu Thr Asp Asn Leu Lys Glu Lys Ala Leu Ser Phe Met Arg Gln Gly
945                 950                 955                 960
Tyr Gln Arg Glu Leu Leu Tyr Gln Arg Glu Asp Gly Ser Phe Ser Ala
                965                 970                 975
Phe Gly Asn Tyr Asp Pro Ser Gly Ser Thr Trp Leu Ser Ala Phe Val
            980                 985                 990
Leu Arg Cys Phe Leu Glu Ala Asp Pro Tyr Ile Asp Ile Asp Gln Asn
        995                1000                1005
Val Leu His Arg Thr Tyr Thr Trp Leu Lys Gly His Gln Lys Ser
    1010                1015                1020
Asn Gly Glu Phe Trp Asp Pro Gly Arg Val Ile His Ser Glu Leu
    1025                1030                1035
Gln Gly Gly Asn Lys Ser Pro Val Thr Leu Thr Ala Tyr Ile Val
    1040                1045                1050
Thr Ser Leu Leu Gly Tyr Arg Lys Tyr Gln Pro Asn Ile Asp Val
    1055                1060                1065
Gln Glu Ser Ile His Phe Leu Glu Ser Glu Phe Ser Arg Gly Ile
    1070                1075                1080
Ser Asp Asn Tyr Thr Leu Ala Leu Ile Thr Tyr Ala Leu Ser Ser
    1085                1090                1095
Val Gly Ser Pro Lys Ala Lys Glu Ala Leu Asn Met Leu Thr Trp
    1100                1105                1110
Arg Ala Glu Gln Glu Gly Gly Met Gln Phe Trp Val Ser Ser Glu
    1115                1120                1125
Ser Lys Leu Ser Asp Ser Trp Gln Pro Arg Ser Leu Asp Ile Glu
    1130                1135                1140
Val Ala Ala Tyr Ala Leu Leu Ser His Phe Leu Gln Phe Gln Thr
    1145                1150                1155
```

-continued

| | | | | | | | | | | | |
|---|---|---|---|---|---|---|---|---|---|---|---|
|Ser|Glu|Gly|Ile|Pro|Ile|Met|Arg|Trp|Leu|Ser|Arg|Gln|Arg|Asn|
| |1160| | | |1165| | | |1170| | | | | |

Ser Glu Gly Ile Pro Ile Met Arg Trp Leu Ser Arg Gln Arg Asn
    1160            1165            1170

Ser Leu Gly Gly Phe Ala Ser Thr Gln Asp Thr Thr Val Ala Leu
    1175            1180            1185

Lys Ala Leu Ser Glu Phe Ala Ala Leu Met Asn Thr Glu Arg Thr
    1190            1195            1200

Asn Ile Gln Val Thr Val Thr Gly Pro Ser Ser Pro Ser Pro Val
    1205            1210            1215

Lys Phe Leu Ile Asp Thr His Asn Arg Leu Leu Leu Gln Thr Ala
    1220            1225            1230

Glu Leu Ala Val Val Gln Pro Met Ala Val Asn Ile Ser Ala Asn
    1235            1240            1245

Gly Phe Gly Phe Ala Ile Cys Gln Leu Asn Val Val Tyr Asn Val
    1250            1255            1260

Lys Ala Ser Gly Ser Ser Arg Arg Arg Arg Ser Ile Gln Asn Gln
    1265            1270            1275

Glu Ala Phe Asp Leu Asp Val Ala Val Lys Glu Asn Lys Asp Asp
    1280            1285            1290

Leu Asn His Val Asp Leu Asn Val Cys Thr Ser Phe Ser Gly Pro
    1295            1300            1305

Gly Arg Ser Gly Met Ala Leu Met Glu Val Asn Leu Leu Ser Gly
    1310            1315            1320

Phe Met Val Pro Ser Glu Ala Ile Ser Leu Ser Glu Thr Val Lys
    1325            1330            1335

Lys Val Glu Tyr Asp His Gly Lys Leu Asn Leu Tyr Leu Asp Ser
    1340            1345            1350

Val Asn Glu Thr Gln Phe Cys Val Asn Ile Pro Ala Val Arg Asn
    1355            1360            1365

Phe Lys Val Ser Asn Thr Gln Asp Ala Ser Val Ser Ile Val Asp
    1370            1375            1380

Tyr Tyr Glu Pro Arg Arg Gln Ala Val Arg Ser Tyr Asn Ser Glu
    1385            1390            1395

Val Lys Leu Ser Ser Cys Asp Leu Cys Ser Asp Val Gln Gly Cys
    1400            1405            1410

Arg Pro Cys Glu Asp Gly Ala Ser Gly Ser His His His Ser Ser
    1415            1420            1425

Val Ile Phe Ile Phe Cys Phe Lys Leu Leu Tyr Phe Met Glu Leu
    1430            1435            1440

Trp Leu
    1445

<210> SEQ ID NO 3
<211> LENGTH: 4335
<212> TYPE: DNA
<213> ORGANISM: Homo sapiens
<220> FEATURE:
<221> NAME/KEY: CDS
<222> LOCATION: (1)..(4335)
<220> FEATURE:
<221> NAME/KEY: CDS
<222> LOCATION: (1)..(4335)

<400> SEQUENCE: 3

```
atg cag ggc cca ccg ctc ctg acc gcc gcc cac ctc ctc tgc gtg tgc      48
Met Gln Gly Pro Pro Leu Leu Thr Ala Ala His Leu Leu Cys Val Cys
1               5                   10                  15 acc gcc gcg ctg gcc gtg gct ccc ggg cct cgg ttt ctg gtg aca gcc      96
Thr Ala Ala Leu Ala Val Ala Pro Gly Pro Arg Phe Leu Val Thr Ala
```

-continued

```
              20                  25                  30
cca ggg atc atc agg ccc gga gga aat gtg act att ggg gtg gag ctt     144
Pro Gly Ile Ile Arg Pro Gly Gly Asn Val Thr Ile Gly Val Glu Leu
        35                  40                  45 ctg gaa cac tgc cct tca cag gtg act gtg aag gcg gag ctc ctc aag     192
Leu Glu His Cys Pro Ser Gln Val Thr Val Lys Ala Glu Leu Leu Lys
50                  55                  60 aca gca tca aac ctc act gtc tct gtc ctg gaa gca gaa gga gtc ttt     240
Thr Ala Ser Asn Leu Thr Val Ser Val Leu Glu Ala Glu Gly Val Phe
65                  70                  75                  80 gaa aaa ggc tct ttt aag aca ctt act ctt cca tca cta cct ctg aac     288
Glu Lys Gly Ser Phe Lys Thr Leu Thr Leu Pro Ser Leu Pro Leu Asn
                85                  90                  95 agt gca gat gag att tat gag cta cgt gta acc gga cgt acc cag gat     336
Ser Ala Asp Glu Ile Tyr Glu Leu Arg Val Thr Gly Arg Thr Gln Asp
            100                 105                 110 gag att tta ttc tct aat agt acc cgc tta tca ttt gag acc aag aga     384
Glu Ile Leu Phe Ser Asn Ser Thr Arg Leu Ser Phe Glu Thr Lys Arg
        115                 120                 125 ata tct gtc ttc att caa aca gac aag gcc tta tac aag cca aag caa     432
Ile Ser Val Phe Ile Gln Thr Asp Lys Ala Leu Tyr Lys Pro Lys Gln
130                 135                 140 gaa gtg aag ttt cgc att gtt aca ctc ttc tca gat ttt aag cct tac     480
Glu Val Lys Phe Arg Ile Val Thr Leu Phe Ser Asp Phe Lys Pro Tyr
145                 150                 155                 160 aaa acc tct tta aac att ctc att aag gac ccc aaa tca aat ttg atc     528
Lys Thr Ser Leu Asn Ile Leu Ile Lys Asp Pro Lys Ser Asn Leu Ile
                165                 170                 175 caa cag tgg ttg tca caa caa agt gat ctt gga gtc att tcc aaa act     576
Gln Gln Trp Leu Ser Gln Gln Ser Asp Leu Gly Val Ile Ser Lys Thr
            180                 185                 190 ttt cag cta tct tcc cat cca ata ctt ggt gac tgg tct att caa gtt     624
Phe Gln Leu Ser Ser His Pro Ile Leu Gly Asp Trp Ser Ile Gln Val
        195                 200                 205 caa gtg aat gac cag aca tat tat caa tca ttt cag gtt tca gaa tat     672
Gln Val Asn Asp Gln Thr Tyr Tyr Gln Ser Phe Gln Val Ser Glu Tyr
210                 215                 220 gta tta cca aaa ttt gaa gtg act ttg cag aca cca tta tat tgt tct     720
Val Leu Pro Lys Phe Glu Val Thr Leu Gln Thr Pro Leu Tyr Cys Ser
225                 230                 235                 240 atg aat tct aag cat tta aat ggt acc atc acg gca aag tat aca tat     768
Met Asn Ser Lys His Leu Asn Gly Thr Ile Thr Ala Lys Tyr Thr Tyr
                245                 250                 255 ggg aag cca gtg aaa gga gac gta acg ctt aca ttt tta cct tta tcc     816
Gly Lys Pro Val Lys Gly Asp Val Thr Leu Thr Phe Leu Pro Leu Ser
            260                 265                 270 ttt tgg gga aag aag aaa aat att aca aaa aca ttt aag ata aat gga     864
Phe Trp Gly Lys Lys Lys Asn Ile Thr Lys Thr Phe Lys Ile Asn Gly
        275                 280                 285 tct gca aac ttc tct ttt aat gat gaa gag atg aaa aat gta atg gat     912
Ser Ala Asn Phe Ser Phe Asn Asp Glu Glu Met Lys Asn Val Met Asp
290                 295                 300 tct tca aat gga ctt tct gaa tac ctg gat cta tct tcc cct gga cca     960
Ser Ser Asn Gly Leu Ser Glu Tyr Leu Asp Leu Ser Ser Pro Gly Pro
305                 310                 315                 320 gta gaa att tta acc aca gtg aca gaa tca gtt aca ggt att tca aga    1008
Val Glu Ile Leu Thr Thr Val Thr Glu Ser Val Thr Gly Ile Ser Arg
                325                 330                 335 aat gta agc act aat gtg ttc ttc aag caa cat gat tac atc att gag    1056
Asn Val Ser Thr Asn Val Phe Phe Lys Gln His Asp Tyr Ile Ile Glu
```

```
                340             345             350
ttt ttt gat tat act act gtc ttg aag cca tct ctc aac ttc aca gcc    1104
Phe Phe Asp Tyr Thr Thr Val Leu Lys Pro Ser Leu Asn Phe Thr Ala
        355                 360                 365 act gtg aag gta act cgt gct gat ggc aac caa ctg act ctt gaa gaa    1152
Thr Val Lys Val Thr Arg Ala Asp Gly Asn Gln Leu Thr Leu Glu Glu
370                 375                 380 aga aga aat aat gta gtc ata aca gtg aca cag aga aac tat act gag    1200
Arg Arg Asn Asn Val Val Ile Thr Val Thr Gln Arg Asn Tyr Thr Glu
385                 390                 395                 400 tac tgg agc gga tct aac agt gga aat cag aaa atg gaa gct gtt cag    1248
Tyr Trp Ser Gly Ser Asn Ser Gly Asn Gln Lys Met Glu Ala Val Gln
                405                 410                 415 aaa ata aat tat act gtc ccc caa agt gga act ttt aag att gaa ttc    1296
Lys Ile Asn Tyr Thr Val Pro Gln Ser Gly Thr Phe Lys Ile Glu Phe
            420                 425                 430 cca atc ctg gag gat tcc agt gag cta cag ttg aag gcc tat ttc ctt    1344
Pro Ile Leu Glu Asp Ser Ser Glu Leu Gln Leu Lys Ala Tyr Phe Leu
        435                 440                 445 ggt agt aaa agt agc atg gca gtt cat agt ctg ttt aag tct cct agt    1392
Gly Ser Lys Ser Ser Met Ala Val His Ser Leu Phe Lys Ser Pro Ser
450                 455                 460 aag aca tac atc caa cta aaa aca aga gat gaa aat ata aag gtg gga    1440
Lys Thr Tyr Ile Gln Leu Lys Thr Arg Asp Glu Asn Ile Lys Val Gly
465                 470                 475                 480 tcg cct ttt gag ttg gtg gtt agt ggc aac aaa cga ttg aag gag tta    1488
Ser Pro Phe Glu Leu Val Val Ser Gly Asn Lys Arg Leu Lys Glu Leu
                485                 490                 495 agc tat atg gta gta tcc agg gga cag ttg gtg gct gta gga aaa caa    1536
Ser Tyr Met Val Val Ser Arg Gly Gln Leu Val Ala Val Gly Lys Gln
            500                 505                 510 aat tca aca atg ttc tct tta aca cca gaa aat tct tgg act cca aaa    1584
Asn Ser Thr Met Phe Ser Leu Thr Pro Glu Asn Ser Trp Thr Pro Lys
        515                 520                 525 gcc tgt gta att gtg tat tat att gaa gat gat ggg gaa att ata agt    1632
Ala Cys Val Ile Val Tyr Tyr Ile Glu Asp Asp Gly Glu Ile Ile Ser
530                 535                 540 gat gtt cta aaa att cct gtt cag ctt gtt ttt aaa aat aag ata aag    1680
Asp Val Leu Lys Ile Pro Val Gln Leu Val Phe Lys Asn Lys Ile Lys
545                 550                 555                 560 cta tat tgg agt aaa gtg aaa gct gaa cca tct gag aaa gtc tct ctt    1728
Leu Tyr Trp Ser Lys Val Lys Ala Glu Pro Ser Glu Lys Val Ser Leu
                565                 570                 575 agg atc tct gtg aca cag cct gac tcc ata gtt ggg att gta gct gtt    1776
Arg Ile Ser Val Thr Gln Pro Asp Ser Ile Val Gly Ile Val Ala Val
            580                 585                 590 gac aaa agt gtg aat ctg atg aat gcc tct aat gat att aca atg gaa    1824
Asp Lys Ser Val Asn Leu Met Asn Ala Ser Asn Asp Ile Thr Met Glu
        595                 600                 605 aat gtg gtc cat gag ttg gaa ctt tat aac aca gga tat tat tta ggc    1872
Asn Val Val His Glu Leu Glu Leu Tyr Asn Thr Gly Tyr Tyr Leu Gly
610                 615                 620 atg ttc atg aat tct ttt gca gtc ttt cag gaa tgt gga ctc tgg gta    1920
Met Phe Met Asn Ser Phe Ala Val Phe Gln Glu Cys Gly Leu Trp Val
625                 630                 635                 640 ttg aca gat gca aac ctc acg aag gat tat att gat ggt gtt tat gac    1968
Leu Thr Asp Ala Asn Leu Thr Lys Asp Tyr Ile Asp Gly Val Tyr Asp
                645                 650                 655 aat gca gaa tat gct gag agg ttt atg gag gaa aat gaa gga cat att    2016
Asn Ala Glu Tyr Ala Glu Arg Phe Met Glu Glu Asn Glu Gly His Ile
```

-continued

```
                   660                 665                 670
gta gat att cat gac ttt tct ttg ggt agc agt cca cat gtc cga aag        2064
Val Asp Ile His Asp Phe Ser Leu Gly Ser Ser Pro His Val Arg Lys
            675                 680                 685 cat ttt cca gag act tgg att tgg cta gac acc aac atg ggt tcc agg        2112
His Phe Pro Glu Thr Trp Ile Trp Leu Asp Thr Asn Met Gly Ser Arg
        690                 695                 700 att tac caa gaa ttt gaa gta act gta cct gat tct atc act tct tgg        2160
Ile Tyr Gln Glu Phe Glu Val Thr Val Pro Asp Ser Ile Thr Ser Trp
705                 710                 715                 720 gtg gct act ggt ttt gtg atc tct gag gac ctg ggt ctt gga cta aca        2208
Val Ala Thr Gly Phe Val Ile Ser Glu Asp Leu Gly Leu Gly Leu Thr
                725                 730                 735 act act cca gtg gag ctc caa gcc ttc caa cca ttt ttc att ttt ttg        2256
Thr Thr Pro Val Glu Leu Gln Ala Phe Gln Pro Phe Phe Ile Phe Leu
            740                 745                 750 aat ctt ccc tac tct gtt atc aga ggt gaa gaa ttt gct ttg gaa ata        2304
Asn Leu Pro Tyr Ser Val Ile Arg Gly Glu Glu Phe Ala Leu Glu Ile
        755                 760                 765 act ata ttc aat tat ttg aaa gat gcc act gag gtt aag gta atc att        2352
Thr Ile Phe Asn Tyr Leu Lys Asp Ala Thr Glu Val Lys Val Ile Ile
770                 775                 780 gag aaa agt gac aaa ttt gat att cta atg act tca aat gaa ata aat        2400
Glu Lys Ser Asp Lys Phe Asp Ile Leu Met Thr Ser Asn Glu Ile Asn
785                 790                 795                 800 gcc aca ggc cac cag cag acc ctt ctg gtt ccc agt gag gat ggg gca        2448
Ala Thr Gly His Gln Gln Thr Leu Leu Val Pro Ser Glu Asp Gly Ala
                805                 810                 815 act gtt ctt ttt ccc atc agg cca aca cat ctg gga gaa att cct atc        2496
Thr Val Leu Phe Pro Ile Arg Pro Thr His Leu Gly Glu Ile Pro Ile
            820                 825                 830 aca gtc aca gct ctt tca ccc act gct tct gat gct gtc acc cag atg        2544
Thr Val Thr Ala Leu Ser Pro Thr Ala Ser Asp Ala Val Thr Gln Met
        835                 840                 845 att tta gta aag gct gaa gga ata gaa aaa tca tat tca caa tcc atc        2592
Ile Leu Val Lys Ala Glu Gly Ile Glu Lys Ser Tyr Ser Gln Ser Ile
850                 855                 860 tta tta gac ttg act gac aat agg cta cag agt acc ctg aaa act ttg        2640
Leu Leu Asp Leu Thr Asp Asn Arg Leu Gln Ser Thr Leu Lys Thr Leu
865                 870                 875                 880 agt ttc tca ttt cct cct aat aca gtg act ggc agt gaa aga gtt cag        2688
Ser Phe Ser Phe Pro Pro Asn Thr Val Thr Gly Ser Glu Arg Val Gln
                885                 890                 895 atc act gca att gga gat gtt ctt ggt cct tcc atc aat ggc tta gcc        2736
Ile Thr Ala Ile Gly Asp Val Leu Gly Pro Ser Ile Asn Gly Leu Ala
            900                 905                 910 tca ttg att cgg atg cct tat ggc tgt ggt gaa cag aac atg ata aat        2784
Ser Leu Ile Arg Met Pro Tyr Gly Cys Gly Glu Gln Asn Met Ile Asn
        915                 920                 925 ttt gct cca aat att tac att ttg gat tat ctg act aaa aag aaa caa        2832
Phe Ala Pro Asn Ile Tyr Ile Leu Asp Tyr Leu Thr Lys Lys Lys Gln
    930                 935                 940 ctg aca gat aat ttg aaa gaa aaa gct ctt tca ttt atg agg caa ggt        2880
Leu Thr Asp Asn Leu Lys Glu Lys Ala Leu Ser Phe Met Arg Gln Gly
945                 950                 955                 960 tac cag aga gaa ctt ctc tat cag agg gaa gat ggc tct ttc agt gct        2928
Tyr Gln Arg Glu Leu Leu Tyr Gln Arg Glu Asp Gly Ser Phe Ser Ala
                965                 970                 975 ttt ggg aat tat gac cct tct ggg agc act tgg ttg tca gct ttt gtt        2976
Phe Gly Asn Tyr Asp Pro Ser Gly Ser Thr Trp Leu Ser Ala Phe Val
```

-continued

```
                          980                 985                 990
     tta  aga  tgt  ttc  ctt  gaa  gcc  gat  cct  tac  ata  gat  att  gat  cag  aat    3024
     Leu  Arg  Cys  Phe  Leu  Glu  Ala  Asp  Pro  Tyr  Ile  Asp  Ile  Asp  Gln  Asn
                          995                 1000                1005 gtg  tta  cac  aga  aca  tac  act  tgg  ctt  aaa  gga  cat  cag  aaa  tcc         3069
     Val  Leu  His  Arg  Thr  Tyr  Thr  Trp  Leu  Lys  Gly  His  Gln  Lys  Ser
          1010                1015                1020 aac  ggt  gaa  ttt  tgg  gat  cca  gga  aga  gtg  att  cat  agt  gag  ctt         3114
     Asn  Gly  Glu  Phe  Trp  Asp  Pro  Gly  Arg  Val  Ile  His  Ser  Glu  Leu
          1025                1030                1035 caa  ggt  ggc  aat  aaa  agt  cca  gta  aca  ctt  aca  gcc  tat  att  gta         3159
     Gln  Gly  Gly  Asn  Lys  Ser  Pro  Val  Thr  Leu  Thr  Ala  Tyr  Ile  Val
          1040                1045                1050 act  tct  ctc  ctg  gga  tat  aga  aag  tat  cag  cct  aac  att  gat  gtg         3204
     Thr  Ser  Leu  Leu  Gly  Tyr  Arg  Lys  Tyr  Gln  Pro  Asn  Ile  Asp  Val
          1055                1060                1065 caa  gag  tct  atc  cat  ttt  ttg  gag  tct  gaa  ttc  agt  aga  gga  att         3249
     Gln  Glu  Ser  Ile  His  Phe  Leu  Glu  Ser  Glu  Phe  Ser  Arg  Gly  Ile
          1070                1075                1080 tca  gac  aat  tat  act  cta  gcc  ctt  ata  act  tat  gca  ttg  tca  tca         3294
     Ser  Asp  Asn  Tyr  Thr  Leu  Ala  Leu  Ile  Thr  Tyr  Ala  Leu  Ser  Ser
          1085                1090                1095 gtg  ggg  agt  cct  aaa  gcg  aag  gaa  gct  ttg  aat  atg  ctg  act  tgg         3339
     Val  Gly  Ser  Pro  Lys  Ala  Lys  Glu  Ala  Leu  Asn  Met  Leu  Thr  Trp
          1100                1105                1110 aga  gca  gaa  caa  gaa  ggt  ggc  atg  caa  ttc  tgg  gtg  tca  tca  gag         3384
     Arg  Ala  Glu  Gln  Glu  Gly  Gly  Met  Gln  Phe  Trp  Val  Ser  Ser  Glu
          1115                1120                1125 tcc  aaa  ctt  tct  gac  tcc  tgg  cag  cca  cgc  tcc  ctg  gat  att  gaa         3429
     Ser  Lys  Leu  Ser  Asp  Ser  Trp  Gln  Pro  Arg  Ser  Leu  Asp  Ile  Glu
          1130                1135                1140 gtt  gca  gcc  tat  gca  ctg  ctc  tca  cac  ttc  tta  caa  ttt  cag  act         3474
     Val  Ala  Ala  Tyr  Ala  Leu  Leu  Ser  His  Phe  Leu  Gln  Phe  Gln  Thr
          1145                1150                1155 tct  gag  gga  atc  cca  att  atg  agg  tgg  cta  agc  agg  caa  aga  aat         3519
     Ser  Glu  Gly  Ile  Pro  Ile  Met  Arg  Trp  Leu  Ser  Arg  Gln  Arg  Asn
          1160                1165                1170 agc  ttg  ggt  ggt  ttt  gca  tct  act  cag  gat  acc  act  gtg  gct  tta         3564
     Ser  Leu  Gly  Gly  Phe  Ala  Ser  Thr  Gln  Asp  Thr  Thr  Val  Ala  Leu
          1175                1180                1185 aag  gct  ctg  tct  gaa  ttt  gca  gcc  cta  atg  aat  aca  gaa  agg  aca         3609
     Lys  Ala  Leu  Ser  Glu  Phe  Ala  Ala  Leu  Met  Asn  Thr  Glu  Arg  Thr
          1190                1195                1200 aat  atc  caa  gtg  acc  gtg  acg  ggg  cct  agc  tca  cca  agt  cct  gta         3654
     Asn  Ile  Gln  Val  Thr  Val  Thr  Gly  Pro  Ser  Ser  Pro  Ser  Pro  Val
          1205                1210                1215 aag  ttt  ctg  att  gac  aca  cac  aac  cgc  tta  ctc  ctt  cag  aca  gca         3699
     Lys  Phe  Leu  Ile  Asp  Thr  His  Asn  Arg  Leu  Leu  Leu  Gln  Thr  Ala
          1220                1225                1230 gag  ctt  gct  gtg  gta  cag  cca  atg  gca  gtt  aat  att  tcc  gca  aat         3744
     Glu  Leu  Ala  Val  Val  Gln  Pro  Met  Ala  Val  Asn  Ile  Ser  Ala  Asn
          1235                1240                1245 ggt  ttt  gga  ttt  gct  att  tgt  cag  ctc  aat  gtt  gta  tat  aat  gtg         3789
     Gly  Phe  Gly  Phe  Ala  Ile  Cys  Gln  Leu  Asn  Val  Val  Tyr  Asn  Val
          1250                1255                1260 aag  gct  tct  ggg  tct  tct  aga  aga  cga  aga  tct  atc  caa  aat  caa         3834
     Lys  Ala  Ser  Gly  Ser  Ser  Arg  Arg  Arg  Arg  Ser  Ile  Gln  Asn  Gln
          1265                1270                1275 gaa  gcc  ttt  gat  tta  gat  gtt  gct  gta  aaa  gaa  aat  aaa  gat  gat         3879
     Glu  Ala  Phe  Asp  Leu  Asp  Val  Ala  Val  Lys  Glu  Asn  Lys  Asp  Asp
```

```
           1280                1285                1290
ctc aat cat gtg gat ttg aat gtg tgt aca agc ttt tcg ggc ccg     3924
Leu Asn His Val Asp Leu Asn Val Cys Thr Ser Phe Ser Gly Pro
    1295                1300                1305 ggt agg agt ggc atg gct ctt atg gaa gtt aac cta tta agt ggc     3969
Gly Arg Ser Gly Met Ala Leu Met Glu Val Asn Leu Leu Ser Gly
1310                1315                1320 ttt atg gtg cct tca gaa gca att tct ctg agc gag aca gtg aag     4014
Phe Met Val Pro Ser Glu Ala Ile Ser Leu Ser Glu Thr Val Lys
    1325                1330                1335 aaa gtg gaa tat gat cat gga aaa ctc aac ctc tat tta gat tct     4059
Lys Val Glu Tyr Asp His Gly Lys Leu Asn Leu Tyr Leu Asp Ser
1340                1345                1350 gta aat gaa acc cag ttt tgt gtt aat att cct gct gtg aga aac     4104
Val Asn Glu Thr Gln Phe Cys Val Asn Ile Pro Ala Val Arg Asn
    1355                1360                1365 ttt aaa gtt tca aat acc caa gat gct tca gtg tcc ata gtg gat     4149
Phe Lys Val Ser Asn Thr Gln Asp Ala Ser Val Ser Ile Val Asp
1370                1375                1380 tac tat gag cca agg aga cag gcg gtg aga agt tac aac tct gaa     4194
Tyr Tyr Glu Pro Arg Arg Gln Ala Val Arg Ser Tyr Asn Ser Glu
    1385                1390                1395 gtg aag ctg tcc tcc tgt gac ctt tgc agt gat gtc cag ggc tgc     4239
Val Lys Leu Ser Ser Cys Asp Leu Cys Ser Asp Val Gln Gly Cys
1400                1405                1410 cgt cct tgt gag gat gga gct tca ggc tcc cat cat cac tct tca     4284
Arg Pro Cys Glu Asp Gly Ala Ser Gly Ser His His His Ser Ser
    1415                1420                1425 gtc att ttt att ttc tgt ttc aag ctt ctg tac ttt atg gaa ctt     4329
Val Ile Phe Ile Phe Cys Phe Lys Leu Leu Tyr Phe Met Glu Leu
1430                1435                1440 tgg ctg                                                         4335
Trp Leu
    1445

<210> SEQ ID NO 4
<211> LENGTH: 1445
<212> TYPE: PRT
<213> ORGANISM: Homo sapiens

<400> SEQUENCE: 4

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
    50                  55                  60

Thr Ala Ser Asn Leu Thr Val Ser Val Leu Glu Ala Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140
```

```
Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
            165                 170                 175

Gln Gln Trp Leu Ser Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
        210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
            245                 250                 255

Gly Lys Pro Val Lys Gly Asp Val Thr Leu Thr Phe Leu Pro Leu Ser
            260                 265                 270

Phe Trp Gly Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
        355                 360                 365

Thr Val Lys Val Thr Arg Ala Asp Gly Asn Gln Leu Thr Leu Glu Glu
        370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
                405                 410                 415

Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
        435                 440                 445

Gly Ser Lys Ser Ser Met Ala Val His Ser Leu Phe Lys Ser Pro Ser
450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
            500                 505                 510

Asn Ser Thr Met Phe Ser Leu Thr Pro Glu Asn Ser Trp Thr Pro Lys
        515                 520                 525

Ala Cys Val Ile Val Tyr Tyr Ile Glu Asp Gly Glu Ile Ile Ser
        530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
```

```
                565                 570                 575
Arg Ile Ser Val Thr Gln Pro Asp Ser Ile Val Gly Ile Val Ala Val
            580                 585                 590

Asp Lys Ser Val Asn Leu Met Asn Ala Ser Asn Asp Ile Thr Met Glu
            595                 600                 605

Asn Val Val His Glu Leu Glu Leu Tyr Asn Thr Gly Tyr Tyr Leu Gly
            610                 615                 620

Met Phe Met Asn Ser Phe Ala Val Phe Gln Cys Gly Leu Trp Val
625                 630                 635                 640

Leu Thr Asp Ala Asn Leu Thr Lys Asp Tyr Ile Asp Gly Val Tyr Asp
            645                 650                 655

Asn Ala Glu Tyr Ala Glu Arg Phe Met Glu Glu Asn Glu Gly His Ile
            660                 665                 670

Val Asp Ile His Asp Phe Ser Leu Gly Ser Ser Pro His Val Arg Lys
            675                 680                 685

His Phe Pro Glu Thr Trp Ile Trp Leu Asp Thr Asn Met Gly Ser Arg
            690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
            725                 730                 735

Thr Thr Pro Val Glu Leu Gln Ala Gln Pro Phe Phe Ile Phe Leu
            740                 745                 750

Asn Leu Pro Tyr Ser Val Ile Arg Gly Glu Glu Phe Ala Leu Glu Ile
            755                 760                 765

Thr Ile Phe Asn Tyr Leu Lys Asp Ala Thr Glu Val Lys Val Ile Ile
            770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
            805                 810                 815

Thr Val Leu Phe Pro Ile Arg Pro Thr His Leu Gly Glu Ile Pro Ile
            820                 825                 830

Thr Val Thr Ala Leu Ser Pro Thr Ala Ser Asp Ala Val Thr Gln Met
            835                 840                 845

Ile Leu Val Lys Ala Glu Gly Ile Glu Lys Ser Tyr Ser Gln Ser Ile
            850                 855                 860

Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
            885                 890                 895

Ile Thr Ala Ile Gly Asp Val Leu Gly Pro Ser Ile Asn Gly Leu Ala
            900                 905                 910

Ser Leu Ile Arg Met Pro Tyr Gly Cys Gly Glu Gln Asn Met Ile Asn
            915                 920                 925

Phe Ala Pro Asn Ile Tyr Ile Leu Asp Tyr Leu Thr Lys Lys Lys Gln
            930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
            965                 970                 975

Phe Gly Asn Tyr Asp Pro Ser Gly Ser Thr Trp Leu Ser Ala Phe Val
            980                 985                 990
```

-continued

Leu Arg Cys Phe Leu Glu Ala Asp Pro Tyr Ile Asp Ile Asp Gln Asn
    995                 1000                1005

Val Leu His Arg Thr Tyr Thr Trp Leu Lys Gly His Gln Lys Ser
    1010                1015                1020

Asn Gly Glu Phe Trp Asp Pro Gly Arg Val Ile His Ser Glu Leu
    1025                1030                1035

Gln Gly Gly Asn Lys Ser Pro Val Thr Leu Thr Ala Tyr Ile Val
    1040                1045                1050

Thr Ser Leu Leu Gly Tyr Arg Lys Tyr Gln Pro Asn Ile Asp Val
    1055                1060                1065

Gln Glu Ser Ile His Phe Leu Glu Ser Glu Phe Ser Arg Gly Ile
    1070                1075                1080

Ser Asp Asn Tyr Thr Leu Ala Leu Ile Thr Tyr Ala Leu Ser Ser
    1085                1090                1095

Val Gly Ser Pro Lys Ala Lys Glu Ala Leu Asn Met Leu Thr Trp
    1100                1105                1110

Arg Ala Glu Gln Glu Gly Gly Met Gln Phe Trp Val Ser Ser Glu
    1115                1120                1125

Ser Lys Leu Ser Asp Ser Trp Gln Pro Arg Ser Leu Asp Ile Glu
    1130                1135                1140

Val Ala Ala Tyr Ala Leu Leu Ser His Phe Leu Gln Phe Gln Thr
    1145                1150                1155

Ser Glu Gly Ile Pro Ile Met Arg Trp Leu Ser Arg Gln Arg Asn
    1160                1165                1170

Ser Leu Gly Gly Phe Ala Ser Thr Gln Asp Thr Thr Val Ala Leu
    1175                1180                1185

Lys Ala Leu Ser Glu Phe Ala Ala Leu Met Asn Thr Glu Arg Thr
    1190                1195                1200

Asn Ile Gln Val Thr Val Thr Gly Pro Ser Ser Pro Ser Pro Val
    1205                1210                1215

Lys Phe Leu Ile Asp Thr His Asn Arg Leu Leu Leu Gln Thr Ala
    1220                1225                1230

Glu Leu Ala Val Val Gln Pro Met Ala Val Asn Ile Ser Ala Asn
    1235                1240                1245

Gly Phe Gly Phe Ala Ile Cys Gln Leu Asn Val Val Tyr Asn Val
    1250                1255                1260

Lys Ala Ser Gly Ser Ser Arg Arg Arg Arg Ser Ile Gln Asn Gln
    1265                1270                1275

Glu Ala Phe Asp Leu Asp Val Ala Val Lys Glu Asn Lys Asp Asp
    1280                1285                1290

Leu Asn His Val Asp Leu Asn Val Cys Thr Ser Phe Ser Gly Pro
    1295                1300                1305

Gly Arg Ser Gly Met Ala Leu Met Glu Val Asn Leu Leu Ser Gly
    1310                1315                1320

Phe Met Val Pro Ser Glu Ala Ile Ser Leu Ser Glu Thr Val Lys
    1325                1330                1335

Lys Val Glu Tyr Asp His Gly Lys Leu Asn Leu Tyr Leu Asp Ser
    1340                1345                1350

Val Asn Glu Thr Gln Phe Cys Val Asn Ile Pro Ala Val Arg Asn
    1355                1360                1365

Phe Lys Val Ser Asn Thr Gln Asp Ala Ser Val Ser Ile Val Asp
    1370                1375                1380

Tyr Tyr Glu Pro Arg Arg Gln Ala Val Arg Ser Tyr Asn Ser Glu
    1385                1390                1395

```
Val Lys Leu Ser Ser Cys Asp Leu Cys Ser Asp Val Gln Gly Cys
    1400                1405                1410

Arg Pro Cys Glu Asp Gly Ala Ser Gly Ser His His His Ser Ser
    1415                1420                1425

Val Ile Phe Ile Phe Cys Phe Lys Leu Leu Tyr Phe Met Glu Leu
    1430                1435                1440

Trp Leu
    1445

<210> SEQ ID NO 5
<211> LENGTH: 2608
<212> TYPE: DNA
<213> ORGANISM: Homo sapiens
<220> FEATURE:
<221> NAME/KEY: Intron
<222> LOCATION: (1)..(951)
<220> FEATURE:
<221> NAME/KEY: exon
<222> LOCATION: (952)..(1069)
<220> FEATURE:
<221> NAME/KEY: Intron
<222> LOCATION: (1070)..(2608)

<400> SEQUENCE: 5
```

| | | |
|---|---|---|
| gtaaaaattt ataaagttct tgcccatac atattttgtt tagtgtttgt tttaaataag | 60 |
| ctttgcccgc tttctaatgt taagtacaa acatagtgta actaagaact aagtagacca | 120 |
| aaaggatttt ttaggaaatg atatttattg aatctaaata cagttttttga taaagccaca | 180 |
| cataaattat ggcaggaagg tctcatcaat gagaagatag gcctttttt tttttttaa | 240 |
| ctgaagggtg atttgactt ccttgaagtc tcatgattct tgttgaagaa aaattgctgg | 300 |
| gagtacattt gttgtcacag gatgggaagc actcatgatt acctcctgtg accctggca | 360 |
| gtgctgctaa ctgaaccctg ctcctcacaa agcattccca ggagtcacag ggagaagggg | 420 |
| catgggtggt ggaaagaatt cagcttggct gataaacccc gtaccacctg gcctgataat | 480 |
| tgagcaggta aatcatgaaa tccacatagt attttatagt cagctgttta aagatacttg | 540 |
| agttaacaca tgagtgaaat ctcaaggaaa caaataacag cattgacagg gatacagaga | 600 |
| aaaacttctg caaatttaga gaaaaaattg gagttaagtt tgaaaatgtg tatttattat | 660 |
| ctataaaaaa tttgtgaaaa aataatgttt attctgaaga tgtaaatttt gcaggaagat | 720 |
| tttattagaa tatggatcaa tatgcagtat tatgacctta tgatgaccta ttctttgaaa | 780 |
| agttgggatt tactgtttta tacttaaacc ttttaaatgg ttttaaattc agatatgtaa | 840 |
| acaataggaa aaattgaaat tcttccaaaa atagtttaga ttattttggc ttatttcaaa | 900 |
| atgtatcagt tcttggtttt tgatgtttta tatttattat cttgacttca gt tac agg | 958 |
| | Tyr Arg |
| | 1 |
| att tac caa gaa ttt gaa gta act gta cct gat tct atc act tct tgg | 1006 |
| Ile Tyr Gln Glu Phe Glu Val Thr Val Pro Asp Ser Ile Thr Ser Trp | |
|     5                   10                  15 | |
| gtg gct act ggt ttt gtg atc tct gag gac ctg ggt ctt gga cta aca | 1054 |
| Val Ala Thr Gly Phe Val Ile Ser Glu Asp Leu Gly Leu Gly Leu Thr | |
|     20                  25                  30 | |
| act act cca gtg gag gtattgtatt aaagagctgc ttatcagtat tacggtgaca | 1109 |
| Thr Thr Pro Val Glu | |
|     35 | |
| ttaagctaat acagcgtcag ctcctcaatt ttttttttaa atgactgctt ataatgttta | 1169 |
| tcacagttta gagattcctt ggctttgtct ttaggttttt atctgtttta tatttaagaa | 1229 |

```
tgtgagctat atatagctat ataaactgct aaatgtgcaa agtccgtatt aagatttggg      1289
tagaaaagtt tattattgac ctgaactaac catctccaaa ggccagaaga gagagaaaga      1349 aaagagaga gagagaaaga ggagaggaga gagagagtga gtctttctat tgtcctctt       1409 caagaatgaa cagaacttct caagatgttc cctagccaat attccatcat gtcttttggt      1469
caaattgcat catatattgt ttcctaagcc agtcactggc aggaggaata taatgaccat      1529
gagtggcctg aattttctca tttgaaattg aaatgtaatt ttgatttaca aaataatcgt      1589
attcatgaaa aatacagtgt agattgaaaa atgctttggg tttatataga aattggaatt      1649
agattgtaag ctcaggccac tataaacaga caattcagca acatgaatgt ctgaagggac      1709
attcaagaat cattaggaac atggggcaat ttttcattgt ctgggctgt cctgagtatt      1769 gcagactgtc acccactaac tacctatagc accttcgagt catggtgaca atctaagaca      1829
ccttcacaaa tgtgcagata aactctagag ggagttactg ctgccagcaa aaccactggc      1889
ctaaactaac ccaggtttag ctttagatgc aggtgtgggg cttggccttt tctgtaggac      1949
ttggccaaca atatcagaat tgggtcactg aggaggaagc acatgtattc agatgtccca      2009
cacattttct catctgtatg taaaaataaa tcatatatat gttttagaaa taatttccaa      2069
tttcctcttt aaatttagtc aggaagcaca tgtattcaga tgtcccacac tagaacaggg      2129
gctgttggat ttggcagggc ttttaaagca gattggtgga gtcaatacag catgaaagaa      2189
gagcaaattg cttcgggatt agacaggctg ggttctagtt ctggctcctc tacttgccag      2249
caatatgaat ttgtactagt tacaaaaatc tcaaaaattt aattttcttt tctataaact      2309
aggagactaa cagtaacctt atggggttgt aataaccaaa caaaataatt tatgtgaagt      2369
gtttggttgc tataaggcac ttaataaagt atagcaatta ttatgttaag taacataaat      2429
caagtcaatt tgccgtcatt catttgtgat aagttgctgt ttgctttctg ttgatagcaa      2489
gttgacattt ctagctgaag ttaaaagctt cacaggtttt ataaagattg catttaattg      2549
cataaaatgt gaagaatttt gacctgaata aaaatatgta ctcgttgtgt tctttccag      2608
```

<210> SEQ ID NO 6
<211> LENGTH: 23
<212> TYPE: DNA
<213> ORGANISM: Homo sapiens

<400> SEQUENCE: 6
ttcaaattct tggtaaatcc tgt                                              23

<210> SEQ ID NO 7
<211> LENGTH: 23
<212> TYPE: DNA
<213> ORGANISM: Homo sapiens

<400> SEQUENCE: 7
ttcaaattct tggtaaatcc tgg                                              23

<210> SEQ ID NO 8
<211> LENGTH: 22
<212> TYPE: DNA
<213> ORGANISM: Homo sapiens

<400> SEQUENCE: 8
atgaccttat gatgacctat tc                                               22

<210> SEQ ID NO 9
<211> LENGTH: 18
<212> TYPE: DNA

<213> ORGANISM: Homo sapiens

<400> SEQUENCE: 9
tttagattat tttggctt                                              18

<210> SEQ ID NO 10
<211> LENGTH: 18
<212> TYPE: DNA
<213> ORGANISM: Homo sapiens

<400> SEQUENCE: 10
atggttagtt caggtcaa                                              18

<210> SEQ ID NO 11
<211> LENGTH: 27
<212> TYPE: DNA
<213> ORGANISM: Homo sapiens

<400> SEQUENCE: 11
tgtatcagtt cttggttttg tgatgtt                                    27

<210> SEQ ID NO 12
<211> LENGTH: 30
<212> TYPE: DNA
<213> ORGANISM: Homo sapiens

<400> SEQUENCE: 12
ccaagaagtg atagaatcag gtacagttac                                 30

<210> SEQ ID NO 13
<211> LENGTH: 40
<212> TYPE: DNA
<213> ORGANISM: Homo sapiens

<400> SEQUENCE: 13
tattatcttg acttcagtta caggatttac caagaatttg                      40

<210> SEQ ID NO 14
<211> LENGTH: 37
<212> TYPE: DNA
<213> ORGANISM: Homos sapiens

<400> SEQUENCE: 14
tattatcttg acttcagttc caggatttac caagaat                         37

<210> SEQ ID NO 15
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(18)

<400> SEQUENCE: 15
gtagcccagg cagacgcc                                              18

<210> SEQ ID NO 16
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: primer

```
<222> LOCATION: (1)..(20)

<400> SEQUENCE: 16
cgcattgtta cactcttctc                                                    20

<210> SEQ ID NO 17
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(19)

<400> SEQUENCE: 17
gattcttcaa atggacttt                                                     19

<210> SEQ ID NO 18
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(21)

<400> SEQUENCE: 18
tgaattccca atcctggagg a                                                  21

<210> SEQ ID NO 19
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(20)

<400> SEQUENCE: 19
ttcaggaatg tggactctgg                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(20)

<400> SEQUENCE: 20
ctgggagcac ttggttgtca                                                    20

<210> SEQ ID NO 21
<211> LENGTH: 20
<212> TYPE: DNA
<213> ORGANISM: Artificial Sequence
<220> FEATURE:
```

-continued

<223> OTHER INFORMATION: Synthetic construct
<220> FEATURE:
<221> NAME/KEY: primer
<222> LOCATION: (1)..(20)

<400> SEQUENCE: 21
acaatttcag acttctgagg                                              20

<210> SEQ ID NO 22
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(21)

<400> SEQUENCE: 22
gacgaagatc tatccaaaat c                                            21

<210> SEQ ID NO 23
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(22)

<400> SEQUENCE: 23
gtgacaacca ctgttggatc aa                                           22

<210> SEQ ID NO 24
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(20)

<400> SEQUENCE: 24
tacatttctt gaaatacctg                                              20

<210> SEQ ID NO 25
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(18)

<400> SEQUENCE: 25
ggctgtgtca cagagatc                                                18

<210> SEQ ID NO 26
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(20)

```
<400> SEQUENCE: 26
gccacccaag aagtgataga                                                      20

<210> SEQ ID NO 27
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(19)

<400> SEQUENCE: 27
cggcttcaag gaaacatct                                                       19

<210> SEQ ID NO 28
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(22)

<400> SEQUENCE: 28
cagcaacatc taaatcaaag gc                                                   22

<210> SEQ ID NO 29
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(18)

<400> SEQUENCE: 29
cacagccaaa gttccata                                                        18

<210> SEQ ID NO 30
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: primer
<222> LOCATION: (1)..(20)

<400> SEQUENCE: 30
gctaggacct gttgtacacc                                                      20
```

ANTIBODIES FOR DIAGNOSIS AND TREATMENT OF BLOOD PLATELET ALLOIMMUNE DISORDERS

CROSS REFERENCE TO RELATED APPLICATIONS

This application is a divisional of U.S. application Ser. No. 10/471,327, filed Aug. 16, 2004, which is now U.S. Pat. No. 7,741,029 which is a National Stage application based on International Application No. PCT/CA02/00291, filed Mar. 7, 2002, which claims priority to U.S. Provisional Patent Application No. 60/273,941, filed Mar. 7, 2001, the disclosures of which are incorporated herein by reference.

INCORPORATION OF SEQUENCE LISTING

A computer readable form of the sequence listing, "02833_$_{0010}$U2_Sequence_Listing2.txt" (76569 bytes), submitted via EFS-WEB and created on Oct. 13, 2010, is herein incorporated by reference.

FIELD OF THE INVENTION

The present invention provides novel compositions and methods for use in diagnosing the occurrence of certain serious disorders, especially certain bleeding disorders, and novel compositions and methods for use in treating such a disorder, in a person in which the disorder has occurred, and novel compositions and methods for use in avoiding such a disorder, in an individual who is susceptible thereto.

BACKGROUND OF THE INVENTION

Among the disorders, which the invention concerns, are those involving abnormal and excessive bleeding due to destruction of blood platelets ("platelets").

These disorders include, but are not restricted to, post-transfusion purpura ("PTP") and post-transfusion platelet refractoriness ("PTPR"), which are suffered by some persons who receive blood, platelets, leukocyte concentrates, or plasma from other persons by transfusion or the like.

The disorders also include one that is suffered by fetuses and newborns and is known as "neonatal alloimmune thrombocytopenia" ("NATP"). This disorder can cause death of fetuses and serious birth defects or death of newborns. NATP is estimated to affect about 1 in 1000 newborns. In NATP, fetal platelets, which enter the mothers blood stream, induce production in the mother of antibodies directed against fetal platelets. These maternal antibodies then pass with the mothers blood into the fetus and mediate destruction of platelets in the fetus.

A mother, whose fetus or newborn suffers from NATP, is at increased risk of suffering PTP or PTPR.

When platelets from a first human (a "donor") are introduced into the blood system of a second human (a "recipient") by transfusion, through the placenta (in the case of fetal blood entering the mother), or the like, the recipient may mount an immune response against the platelets from the donor. Such an immune response is referred to as an "alloimmune" response, because it involves antibodies reacting against antigens of a different individual of the same species. The alloimmune response to platelets is due to an immune response of the recipient against "alloantigens" (antigens of the same species as that mounting the immune response) on platelets from the donor. These alloantigens are found on membrane glycoproteins that occur in the cell membranes, which define the outer surfaces of platelets ("platelet membranes"). In this invention, the glycoprotein is anchored to the membrane in an atypical manner through an anchor consisting of glycosylphosphatidylinositol (GPI), which anchors an extracellular domain or segment of the glycoprotein exposed to the outside of the platelet. It is thought that alloantibodies, which are generated in an alloimmune response against platelet alloantigens, interact with the extracellular domains of the alloantigens.

The platelet alloantigens that a person has are determined by the person's genetics. A donor, because of his or her genetics, may have a platelet alloantigen, which a recipient, who receives blood, platelets, leukocytes or plasma from the donor, does not have, because of the recipient's genetics. In such a situation, the immune system of the recipient may recognize the donor's alloantigen as "non-self," and raise an immune response against, the platelet alloantigen, which the donor has but the recipient does not.

Membrane glycoprotein alloantigens have been characterised for both human red blood cells and human platelets. It is noteworthy, however, that they also occur on other cell types, such as leukocytes and endothelial cells, where they may also occasion various disorders through alloimmune responses.

Recognised classes of red blood cell and platelet alloantigens have been described, over the past 30 years, based on observations of antibody reactions occurring when blood recipients have been exposed to blood from donors.

A recent review of human platelet alloantigen systems is provided by Ouwehand, W., and Navarrete, C., in *Molecular Haematology*, Provan, D. and Gribben, J. eds. Blackwell (1999).

Several biallelic platelet alloantigen "systems" have been characterised. In each of these systems, there are two alloantigens, each of which is provided by one of two alleles of the gene comprising the system. Because each gene occurs twice in the normal human genome, a person can be homozygous for one or the other of the two alloantigens, or heterozygous for the two alloantigens, comprising a biallelic system. The alloantigens described to date occur on glycoprotein molecules which may exist in various forms (transmembrane, GPI-linked and soluble, for example). In such a case, the alloantigens are found on each of the variant forms of the glycoprotein. For all of the biallelic platelet alloantigen systems that have been characterised at the level of protein and gene sequences, it has been found in all cases, except for one, that the difference between the two alleles is based on a single nucleotide polymorphism in the relevant gene.

One biallelic system of human platelet alloantigens is the Gov$^a$/Gov$^b$ biallelic system associated with CD109, a membrane glycoprotein which occurs on platelets and various other cell types, including leukocytes and endothelial cells. Each Gov allele corresponds to one CD109 glycoprotein (Sutherland, D. R. et al, 1991; Smith et al., 1995; Berry, J. et al., 2000), consistent with the known tissue distribution of CD109. The frequencies for the Gov alleles are 0.4 for Gov$^a$ and 0.6 for Gov$^b$ in the Caucasian population. Thus, in this population, 40.7% are heterozygous for the Gov alleles, and will not mount an alloimmune response due to Gov incompatibility (not possessing the Gov alloantigen found on platelets received from another). In contrast, 19.8% of Caucasians are homozygous for the Gov$^a$ allele and thus may mount an immune response due to Gov alloantigen incompatibility against platelets received from anyone in the 80.5% of the Caucasian population that is not homozygous for the Gov$^a$ allele, while 39.8% are homozygous for the Gov$^b$ allele and thus may mount an immune response due to Gov alloantigen incompatibility against platelets received from anyone in the 60.2% of the Caucasian population that is not homozygous for the Gov$^b$ allele.

As indicated above, alloimmunization based on Gov incompatibility (the introduction into the blood stream of donor platelets bearing a Gov alloantigen not carried by the recipient) can result in bleeding disorders due to platelet destruction, including NATP, PTPR, and PTP. The location of the Gov antigens within the CD109 molecule, and the nature of the CD109 polymorphism which underlies the Gov$^a$/Gov$^b$ alloantigen (both at the protein and at the gene level), have not heretofore been known.

Furthermore, it has not heretofore been possible to generate non-human antibody (polyclonal or monoclonal), as from a rat, mouse, goat, chicken, or the like, with specificity for the Gov$^a$ alloantigen but not the Gov$^b$ alloantigen (or vice-versa) sufficient for use in an immunoassay, for typing for Gov phenotype using platelets or CD109 molecules.

Previously developed technology, involving gene-specific amplification of platelet RNA-derived cDNA, followed by the determination of the nucleotide sequence of the amplified DNA, has been applied successfully to the elucidation of the molecular basis of other biallelic platelet alloantigen systems (Newman et al., J. Clin. Invest. 82, 739-744 (1988); Newman et al., J. Clin. Invest. 83, 1778-1781 (1989) (P1A or HPA-1 system); Lyman et al., Blood 75, 2343-2348 (1990) (Bak or HPA-3system); Kuijpers et al., J. Clin. Invest. 89, 381-384 (1992) (HPA-2 or Ko system); Wang et al., J. Clin. Invest. 90, 2038-2043 (1992) (Pen system). With one exception, it has been found in each case that a single amino acid difference at a single position differentiates the amino acid sequences of the two alleles, and that this difference arises from a single allele-specific nucleotide substitution in the coding region of the mRNA and gene. There remains a need to elucidate the molecular basis of the biallelic Gov platelet alloantigen system.

SUMMARY OF THE INVENTION

The Gova/Govb Cd109 Single Nucleotide Polymorphism

We have now discovered that a single amino acid difference in the CD109 glycoprotein distinguishes the Gov$^a$ and Gov$^b$ allelic forms. The two alleles differ at amino acid position 703 of the full-length 1445 amino acid CD109 molecule, with the Gov$^a$ allele [SEQ ID NO:2] containing a Tyr at this position, while the Gov$^b$ allele [SEQ ID NO:4] contains Ser.

Further, we have discovered that this difference in amino acid sequence between the allelic forms of CD109 is due to a single nucleotide polymorphism at position 2108 of the coding portion of full-length mRNA encoding CD109, or of the corresponding coding strand of the cDNA corresponding to this mRNA. Specifically, the Gov$^a$ allele [SEQ ID NO:1] contains adenine at position 2108, the second nucleotide of the codon encoding the amino acid at position 703 of the full-length CD109 protein, while the Gov$^b$ allele contains cytosine at position 2108, as shown in SEQ ID NO:3

The Gov$^a$/Gov$^b$ single nucleotide polymorphism of CD109, lies at position 2108 in SEQ ID NO:1. SEQ ID NO:1 is the cDNA sequence encoding the full-length 1445 amino acid CD109 precursor encoding the Gov$^a$ allele In the Gov$^b$ allele form [SEQ ID NO:3], C occurs at position 2108, rather than A. The ATG at the 5'-end of the sequence in SEQ ID NO:1 corresponds to the translation start of the full-length precursor form (including leader peptide) of CD109. The triplet corresponding to the N-terminal amino acid of the mature CD109 protein is at positions 64-66 in SEQ ID NO:1.

The Gov$^a$/Gov$^b$ single nucleotide polymorphism of CD109, lies at position 954 in SEQ ID NO:5. SEQ ID NO:5 is the genomic DNA sequence of human CD109 exon 19 and the contiguous introns, introns 18 and 19. The Gov$^a$/Gov$^b$ single nucleotide polymorphism of CD109 is found within CD109 exon 19, and specifically is located at position 3 of CD109 exon 19. The sequence presented in SEQ ID NO:5 contains A at position 954, and thus corresponds to the Gov$^a$ allele. The corresponding Gov$^b$ sequence contains C at position 954 of SEQ ID NO:5 (nucleotide position 3 of exon 19).

In view of this discovery, it will be readily apparent to the skilled what the present invention provides:

Gov allele-specific oligonucleotides and polynucleotides: Based on the discovery, the present invention provides oligonucleotides and polynucleotides (seems repetitive), including (but not limited to) probes which can be used to determine whether a person is homozygous for one or the other of the Gov alleles, or heterozygous for these alleles, thereby to determine that person's Gov genotype, and by extension, their Gov phenotype (i.e., the Gov alloantigen(s) which their cells express). Further, the invention provides methods of using such oligonucleotides, and test kits to facilitate their use, in such Gov genotype and phenotype determinations. These oligonucleotides of the invention can be used to determine whether, in the CD109 gene, or in the mRNA encoding CD109, the internal nucleotide (nucleotide 2108) of the codon (in CD109 gene or in the mRNA encoding CD109) which corresponds to the amino acid at position 703 in the sequence of full-length CD109 is adenine or cytosine. Such probes will typically be cDNA but may be genomic DNA, mRNA or RNA, and may be labelled for detection. The oligonucleotides of the invention can be used as probes to detect nucleic acid molecules according to techniques known in the art (for example, see U.S. Pat. Nos. 5,792,851 and 5,851,788).

For example, an oligonucleotide of the invention may be converted to a probe by being end-labelled using digoxigenin-11-deoxyuridine triphosphate. Such probes may be detected immunologically using alkaline-phosphate-conjugated polyclonal sheep antidigoxigenin F(ab) fragments and nitro blue tetrazolium with 5-bromo-4-chloro-3-indoyl phosphate as chromogenic substrate.

Gov allele-specific antibodies: Still further, based on the discovery, which underlies the invention, of the molecular basis for the Gov$^a$/Gov$^b$ alloantigen system, the invention provides non-human polyclonal and monoclonal antibodies, which can be used to distinguish one Gov allelic form of CD109 from the other, whether the CD109 is part of a complex embedded in or isolated from a membrane or is isolated. These antibodies of the invention, which are preferably provided in an aqueous buffer solution, and the immunoassays of the invention which employ such antibodies, are useful for determining whether a person has one or both of the Gov alloantigens and for Gov phenotyping. Methods of using the antibodies of the invention in the immunoassays of the invention, and in such determinations, are also encompassed by the invention. The invention also provides test kits to facilitate carrying out such immunoassays and determinations.

Gov allele-specific peptides and polypeptides: Again, based on the discovery that underlies the invention, of the molecular basis for the Gov$^a$/Gov$^b$ alloantigen system, the invention provides peptides or polypeptides, which are useful for various purposes. These peptides or polypeptides are typically between 4 and 100, and more typically between 7 and 50, amino acids in length, and have amino acid sequences identical or having sequence identity to those of segments of the CD109 sequences, that include the amino acid at position 703 of full-length mature CD109. This amino acid (position 703) corresponds to the triplet at positions 2107-2109 in the CD109 cDNA sequence presented in SEQ ID NO:1, or in the corresponding sequence for the CD109 cDNA that encodes the $Gov^b$ allelic form [SEQ ID NO:3]. These peptides or polypeptides may be synthetic, may be purified from native CD109 or may be prepared by recombinant means. For guidance, one may consult the following U.S. Pat. Nos. 5,840,537, 5,850,025, 5,858,719, 5,710,018, 5,792,851, 5,851,788, 5,759,788, 5,840,530, 5,789,202, 5,871,983, 5,821,096, 5,876,991, 5,422,108, 5,612,191, 5,804,693, 5,847,258, 5,880,328, 5,767,369, 5,756,684, 5,750,652, 5,824,864, 5,763,211, 5,767,375, 5,750,848, 5,859,337, 5,563,246, 5,346,815, and WO9713843. Many of these patents also provide guidance with respect to experimental assays, probes and antibodies, methods, transformation of host cells, which are described below. These patents, like all other patents, publications (such as articles and database publications) in this application, are incorporated by reference in their entirety.

Gov allele-specific peptides and polypeptides as antigens and immunogens, and Gov allele-specific polyclonal and monoclonal antibodies: These peptides or polypeptides are useful as antigens (usually coupled to a larger, immunogenic carrier [proteinaceous or otherwise], as known in the art) for making the polyclonal or monoclonal antibodies of the invention. The peptides or polypeptides are also useful in screening monoclonal antibody-producing cultures (hybridoma cultures/E. coli cultures or so-called V gene phage antibodies) to identify those that produce monoclonal antibodies of the invention.

The invention also encompasses immunogenic compositions which comprise a peptide, polypeptide or fusion compound of the invention and which are immunogenic in a bird, including, without limitation, a chicken, or a mammal, such as, a mouse, rat, goat, rabbit, guinea pig, sheep or human. The compositions may include an immunogenicity-imparting "carrier" which may be but is not necessarily a protein as known in the art, that is immunogenic in a bird or mammal, coupled to at least one peptide or polypeptide of the invention, which has an amino acid sequence that is the same as that of a segment of the sequence for CD109, that includes the amino acid at position 703 of the full length CD109 molecule.

The present invention also provides methods of using the peptides, polypeptides and immunogenic compositions of the invention for making antibodies of the invention, and methods of using the peptides and polypeptides of the invention in screening monoclonal antibody-producing hybridoma cultures or bacterial clones for those that produce monoclonal antibodies or fragments thereof of the invention.

Therapeutic and diagnostic application of Gov allele-specific peptides, polypeptides, and antibodies: These peptides or polypeptides, as well as antibodies, which are specific for the $Gov^a$ [SEQ ID NO:2] or $Gov^b$ [SEQ ID NO:4], but not both, allelic forms of CD109 in the platelet membrane, and which can be produced by a mammal (including an human) immunized with the peptides or polypeptides, which themselves happen to be immunogenic, or the immunogenic compositions of the invention, are also useful both therapeutically and diagnostically. The invention also provides the methods of using the peptides and polypeptides of the invention, and antibodies made using the peptides that are immunogenic and the immunogenic compositions of the invention, in therapeutic and diagnostic applications.

The Gov allele-specific peptides or polypeptides can also be used diagnostically to detect the presence of $Gov^a$ or $Gov^b$ specific antibodies in human plasma or serum samples, using methods that are readily apparent to those skilled in the art.

Such analyses would be useful in the investigation of cases of acquired alloimmune thrombocytopenia, including PTP, PTPR, and NATP. In the latter case, this approach could also be used to detect the presence of Gov allele-specific antibodies in the mother of the affected fetus or newborn. The presence of Gov allele-specific antibodies can also be detected using platelets of known Gov phenotype. However, this approach has numerous technical disadvantages that are eliminated by the use of Gov allele-specific peptides or polypeptides for Gov allele-specific antibody detection.

Administration to a person, who is suffering from, or at risk for, for example, PTP or PTPR, or a mother at risk for passing NATP-causing alloantibodies to her fetus, of one of the peptides or polypeptides, that would be bound by the anti-Gov alloantibodies in such a person, would inhibit the binding of the alloantibodies to the person's (or the fetus's platelets and thereby inhibit the platelet destruction and abnormal bleeding associated with the disorders. Alternatively, administration to such a person of antibodies (particularly human antibodies), which are produced using a peptide or polypeptide of the invention, which is immunogenic by itself, or an immunogenic composition of the invention, and which are specific for the Gov allelic form of the CD109 on the person's platelets which is associated with the PTP or PTPR, from which the person is suffering or may suffer, would induce the production of anti-idiotypic antibodies, which, in turn, would inhibit the platelet-destructive effects of the anti-Gov alloantibodies, which are generated by the person's own immune system and which are causing or threatening to cause the PTP, PTPR or NATP. These therapeutic applications of peptides and polypeptides of the invention would be especially useful in treating NATP in a newborn, because the alloantibody giving rise to NATP in the newborn is not continuously produced by the immune system of the newborn, but rather is acquired passively, and therefore in limited, non-replenished quantity, by the newborn from its mother.

Thus, in accordance with one aspect of the present invention, an oligonucleotide probe is provided that hybridizes to a portion of the CD109 gene, or a portion of CD109-encoding mRNA or cDNA prepared from such mRNA, which portion includes a nucleotide corresponding to the internal nucleotide of the codon for the amino acid at position 703 of the full-length CD109 molecule, and that is capable of distinguishing one Gov allele from the other through the ability to hybridize under stringent conditions to the portion in question only when the nucleotide in question is A (or dA), when the probe is to detect the $Gov^a$ allele, or C (or dC), when the probe is to detect the $Gov^b$ allele. The nucleotide in question is at position 2108 of the coding region of the CD109 cDNA sequence and lies at position 2108 in SEQ ID NO:1. The cDNA sequence has A at this position, and so is the sequence corresponding to the $Gov^a$ allele. The nucleotide in question lies at position 954 of the sequence presented as SEQ ID NO:5 and contains an A in this position, and thus also corresponds to $Gov^a$ allele.

The Gov allele-specific oligonucleotide hybridization probes of the invention may comprise genomic DNA, cDNA, or RNA, although preferably it is DNA. Such oligonucleotide probes can be synthesised by automated synthesis and will preferably contain about 10-30 bases, although as understood in the oligonucleotide probe hybridization assay art, as few as 8 and as many as about 50 nucleotides may be useful, depending on the position within the probe where the potential mismatch with the target is located, the extent to which a label on the probe might interfere with hybridization, and the physical conditions (e.g., temperature, pH, ionic strength) under which the hybridization of probe with target is carried out.

In accordance with another aspect of the present invention, a test kit for Gov alloantigen typing is provided comprising:
(a) means for amplifying nucleic acid that comprises at least a portion of a CD109 gene, a CD109-encoding mRNA, or a CD109 cDNA made from such RNA, wherein the portion includes a nucleotide (nucleotide 2108 in SEQ ID NO:1, or nucleotide 954 in SEQ ID NO:5) corresponding to the internal nucleotide of the codon encoding amino acid 703 of the full length CD109 protein.
(b) an oligonucleotide probe of the invention, that distinguishes one Gov allele from the other. The "means for amplifying" will, as the skilled will readily understand, depend on the amplification method to be used. Thus, for example, these means might include suitable primers, a suitable DNA polymerase, and the four 2'-deoxyribonucleoside triphosphates (dA, dC, dG, dT), if amplification is to be by the PCR method. To cite another example, if the amplification is to be by a method relying on transcription, such as the 3SR method, the means will include two primers, at least one of which, when made double-stranded, will provide a promoter, an RNA polymerase capable of transcribing from that promoter, a reverse transcriptase to function in primer-initiated, DNA-directed and RNA-directed, DNA polymerization and possibly also in RNAse H degradation of RNA to free DNA strands from RNA/RNA hybrids, the four ribonucleoside triphosphates (A, C, G and U), and the four 2'-deoxyribonucleoside triphosphates. In another example, if the amplification is by the ligase chain reaction, the means will include two oligonucleotides (DNAs) and a suitable DNA ligase that will join the two if a target, to which both can hybridize adjacent to one another in ligatable orientation, is present.

The oligonucleotide probes of the invention will preferably be labelled. The label may be any of the various labels available in the art for such probes, including, but not limited to $^{32}P$; $^{35}S$; biotin (to which a signal generating moiety, bound to or complexed with avidin can be complexed); a fluorescent moiety; an enzyme such as alkaline phosphatase (which is capable of catalysing a chromogenic reaction); digoxigenin, as described above; or the like.

As indicated in the examples, RFLP analysis can be employed, using BstNI (or isoschizomers thereof), in analysing cDNA or genomic DNA (with or without amplification) to determine Gov genotype. As indicated further in the examples, electrophoretic SSCP analysis may be used to determine Gov genotype. And as indicated in the examples, the hybridization studies outlined above may use fluorescent probes, and may be directly coupled to the DNA amplification step, as in "Real-Time PCR" or related methods.

There has also been provided, in accordance with another aspect of the present invention, a method of typing for Gov allele-specific target sequence in a CD109 nucleic acid derived from a subject, comprising the steps of,
(a) obtaining, by a target nucleic acid amplification process applied to mRNA from human platelets, endothelial cells, or T cells, an assayable quantity of amplified nucleic acid with a sequence that is that of a subsequence (or the complement of a subsequence) of the mRNA that encodes a CD109 said subsequence including the nucleotide at the position in the mRNA corresponding to position 2108 in SEQ ID NO:1 or to nucleotide 954 in SEQ ID NO:5; and
(b) analyzing (e.g., in a nucleic acid probe hybridization assay employing an oligonucleotide probe or probes according to the invention) the amplified nucleic acid obtained in step (a) to determine the base or bases at the position in the amplified nucleic acid that corresponds to position 2108 in SEQ ID NO:1 or to nucleotide 954 in SEQ ID NO:5. It is noteworthy that, if the product of the amplification is double-stranded DNA, analysis for Gov genotype can be carried out by a RFLP (restriction fragment length polymorphism) analysis comprising exposing the amplified DNA to the restriction endonuclease BstNI (or isoschizomer thereof) under conditions whereby the DNA will be cleaved if it includes a site for cleavage by that enzyme. Such DNA, prepared from mRNA encoding the $Gov^b$ alloantigen, containing a C rather than an A at the position corresponding to nucleotide 2108 in SEQ ID NO:1 (or to nucleotide 954 in SEQ ID NO:5), includes a recognition site for that endonuclease, while such DNA prepared from mRNA encoding the $Gov^a$ alloantigen, does not. If the analysis, by whatever method, of the amplified nucleic acid reveals that there is only an A (or dA) at the position corresponding to position 12108, the platelets (and blood from which they came) have only the $Gov^a$ alloantigen, and the individual from whom the platelets came, is homozygous for $Gov^a$. Alternatively, if the analysis of the amplified nucleic acid reveals that there is only a C (or dC) at the position corresponding to position 2108, the platelets (and blood from which they came) have only the $Gov^b$ alloantigen and the individual, from whom the platelets came, is homozygous for the $Gov^b$ allele. Finally, if the analysis indicates that there is either an A (or dA) or a C (or dC) at that position, the platelets (and blood from which they came) have both Gov alloantigens, and the individual from whom the platelets came, is heterozygous for Gov alloantigen.

In one application of the typing methods of the invention, the methods are applied to two individuals to determine whether blood or platelets from one would provoke an alloimmune response, and possibly PTP or PTPR, in the other. The typing method can be applied with a man and a woman, who are contemplating conceiving or have conceived a child together, to determine the risk that the child would be at risk for NATP and the risk that the woman would be at increased risk for PTP or PTPR. If the woman were heterozygous for the Gov alloantigens there would be, due to Gov alloantigen incompatibility, no risk of NATP and no increased risk for the woman of PTP or PTPR. If, however, the woman were homozygous for one of the Gov alloantigens, there would be, due to Gov alloantigen incompatibility, risk of NATP in a child and increased risk of PTP or PTPR for the woman, unless the man is homozygous for the same Gov alloantigen as is the woman.

In accordance with yet another aspect of the present invention, a method of typing an individual for Gov alloantigen is provided that comprises analyzing the genomic DNA of the individual to determine the Gov alloantigen(s) of the individual. Applications of this method are substantially the same as those of the method of the invention for typing for Gov alloantigen that begins with platelet, endothelial cell, or T cell mRNA.

This method of the invention, entailing analysis of genomic DNA, can be carried out in substantially the same way as outlined above for analysis of mRNA, namely first amplifying the genomic DNA and then analyzing to product of the amplification to ascertain whether there is only dA, only dC, or both dA and dC, at the position in the coding region of the genomic DNA corresponding to position 2108 in SEQ ID NO:1, or to nucleotide 954 in SEQ ID NO:5.

In accordance with a further aspect of the present invention, a test kit for Gov alloantigen typing is provided comprising a non-human antibody (or antibodies) that distinguishes the two allelic forms of CD109. The antibody (or antibodies) of the kit may be polyclonal, or preferably monoclonal, and in addition to its (their) specificity for either but not both Gov alloantigens (on the surface of platelets or separated therefrom) or the CD109 subunit of one but not both of such alloantigens, typically will recognise a polypeptide molecule encoded by a nucleotide sequence encoding at least amino acid 703 of a CD109 polypeptide (the amino acid at the position corresponding to nucleotides 2107-2109 in SEQ ID NO:1, or to nucleotides 953-955 in SEQ ID NO:5).

The invention relates to an oligonucleotide comprising a sequence which binds specifically to (i) a region of CD109 nucleic acid that includes a single nucleotide polymorphism that is distinctive of a Gov$^a$ allele and/or (ii) a region of CD109 nucleic acid that includes a single nucleotide polymorphism that is distinctive of a Gov$^b$ allele. The oligonucleotide optionally comprises 8 to 50 nucleotides. The oligonucleotide preferably specifically binds to one of (i) or (ii) under high stringency hybridization conditions. The stringent hybridization conditions optionally comprise 0.1×SSC, 0.1% SDS at 65° C. The CD109 nucleic acid optionally comprises genomic DNA, cDNA, or RNA corresponding to the Gov$^a$ allele of the CD109 gene or locus, or comprises genomic DNA, cDNA, or RNA corresponding to the Gov$^b$ allele of the CD109 gene or locus. The Gov$^a$ allele optionally comprises an A at a position corresponding to position 2108 of SEQ ID NO:1 and corresponding to position 954 of SEQ ID NO:5. The Gov$^b$ allele optionally comprises a C at a position corresponding to position 2108 of SEQ ID NO:3 and corresponding to position 954 of SEQ ID NO:5. The oligonucleotide optionally comprises a sequence complementary to the Gov$^a$ allele or to the Gov$^b$ allele. The oligonucleotide optionally comprises a sequence selected from the group consisting of:
(a) 8-50 nucleotides of SEQ ID NO:1;
(b) a sequence that is complementary to a sequence specified in (a); and
(c) a sequence having at least 70% sequence identity to a sequence in (a) or (b), wherein the sequence having identity is capable of hybridization to CD109 under high stringency hybridization conditions.

The oligonucleotide optionally comprises a sequence selected from the group consisting of:
(a) 8-50 nucleotides of SEQ ID NO:3;
(b) a sequence that is complementary to a sequence specified in (a); and
(c) a sequence having at least 70% sequence identity to a sequence in (a) or (b), wherein the sequence having identity is capable of hybridization to CD109 under high stringency hybridization conditions.

The oligonucleotide optionally comprises all or part of any one of SEQ ID NO:6-SEQ ID NO:14 or a complement thereof. The oligonucleotide optionally comprises 8 to 50 nucleic acids. The nucleic acid is capable of use as a probe in a hybridization assay. The nucleic acid sequence is typically detectably labelled. The detectable label optionally comprises:
(a) a fluorogenic dye; and/or
(b) a biotinylation modification; and/or
(c) a radiolabel.

The oligonucleotide sequence optionally comprises DNA, a DNA analog, RNA or an RNA analog. The oligonucleotide is optionally attached to a substrate. The oligonucleotide is optionally capable of use as a primer that will specifically bind proximate to, and/or cause elongation through, a CD109 sequence, including the single nucleotide polymorphism distinctive of the Gov$^a$ or Gov$^b$ alleles.

Another aspect of the invention relates to a Gov genotyping kit comprising a detection agent for detecting the presence of a Gov allele-specific target sequence in a CD109 nucleic acid derived from a subject. The detection agent optionally comprises a nucleic acid and/or a restriction enzyme. The kit optionally further comprises a container. The container optionally comprises a biological sample container for housing the detection agent. The kit optionally further comprises a plate having a plurality of wells and having bound thereto probes having a nucleic acid sequence which specifically binds to a CD109 sequence including a Gov$^a$ or a Gov$^b$ allele target sequence. The restriction enzyme is optionally selected from the group consisting of Bst2UI, BstNI, BstOI, EcoRII, MaeIII, MspR91, MvaI, ScrFI or an isoschizomer thereof. The kit optionally further comprises an amplification agent for amplifying the nucleic acid. The amplification agent amplifies a region of CD109 platelet, T cell, or endothelial cell mRNA including the single nucleotide polymorphism distinctive of a Gov$^a$ or Gov$^b$ allele. The amplification agent optionally comprises a primer set including first and second primers, wherein the first primer is a nucleic acid that will specifically bind proximate to, and/or cause elongation through, CD109 sequence that includes the single nucleotide polymorphism distinctive of a Gov$^a$ allele and the second primer is a nucleic acid that will specifically bind proximate to, and/or cause elongation through, CD109 sequence that includes the single nucleotide polymorphism distinctive of a Gov$^b$ allele. The nucleic acid is optionally obtained by amplification with all or part of the nucleic acid of any one of SEQ ID NO:6-SEQ ID NO:14 or the complement thereof. The kit optionally further comprises all or part of a CD109 gene, a CD109-encoding mRNA, or a CD109 cDNA made from a CD109-encoding mRNA. The kit optionally further comprises the oligonucleotide of the invention. The kit is useful for detecting that the subject has or is at risk of a disease, disorder or abnormal physical state, such as a blood disease, disorder or abnormal physical state which in some cases may comprise bleeding of the subject, or increased risk of bleeding, due to destruction of blood platelets. The blood disease, disorder or abnormal physical state will often be post-transfusion purpura ("PTP"), post-transfusion platelet refractoriness ("PR") or neonatal alloimmune thrombocytopenia ("NAIT"). The nucleic acid for the kit and methods is usually obtained from mRNA from human platelets, T cells, endothelial cells, or human genomic DNA.

Another aspect of the invention relates to a method of Gov alloantigen genotyping a subject comprising:
(a) providing a CD109 nucleic acid sample derived from the subject; and
(b) detecting a region of CD109 nucleic acid that includes a single nucleotide polymorphism distinctive of a Gov$^a$ or a Gov$^b$ allele.

The method preferably comprises determining whether the subject is homozygous or heterozygous for the Gov alleles. The subject of the methods will typically be a human and the Gov genotype is used to determine that the subject has, or is at risk of a disease, disorder or abnormal physical state, such as a blood disease, disorder or abnormal physical state for example, comprising bleeding of the subject, or increased risk of bleeding, due to destruction of blood platelets. Examples of blood disease, disorder or abnormal physical state include post-transfusion purpura ("PTP"), post-transfusion platelet refractoriness ("PR") or neonatal alloimmune thrombocytopenia ("NAIT"). The nucleic acid is typically obtained by amplifying the nucleic acid from the subject. The nucleic acid is preferably obtained by amplification with all or part of an oligonucleotide of the invention. The nucleic acid is typically obtained from mRNA from human platelets, T cells, endothelial cells, or human genomic DNA. The detection step optionally comprises determining the nucleotide sequence of the CD109 nucleic acid or contacting the nucleic acid with the oligonucleotide under high stringency conditions. In a hybridization step, the oligonucleotide will optionally selectively hybridize to (i) a region of CD109 nucleic acid that includes a single polymorphism distinctive of a Gov$^a$ allele or (ii) a region of CD109 nucleic acid that includes a single polymorphism distinctive of a Gov$^b$ allele. The detecting step optionally comprises:
(a) performing a restriction endonuclease digestion of the nucleic acid, thereby providing a nucleic acid digest; and
(b) contacting the digest with the oligonucleotide.

Hybridization optionally occurs either during or subsequent to PCR amplification and the analysis is optionally by "Real-Time" PCR analysis, or fluorimetric analysis. The detection step optionally comprises:
(a) incubation of the amplified nucleic acid with a restriction endonuclease under conditions whereby the DNA will be cleaved if the nucleic acid comprises a recognition site for the enzyme; and
(b) determining whether the nucleic acid contains a recognition site for the restriction enzyme characteristic of cDNA made from mRNA encoding a Gov$^a$ or Gov$^b$ allele of CD109.

The restriction enzyme is, for example, selected from the group consisting of Bst2UI, BstNI, BstOI, EcoRII, MaeIII, MspR91, MvaI, ScrFI or an isoschizomer thereof. The determination step optionally includes size analysis of the nucleic acid. The amplified nucleic acid is optionally analyzed by electrophoretic mobility and the mobility of the amplified nucleic acid is compared to the characteristic mobility of amplified nucleic acid fragments corresponding to the Gov$^a$ or Gov$^b$ alleles of CD109. The method of amplifying CD109 mRNA optionally comprises amplifying the mRNA by PCR using an oligonucleotide of the invention.

Another aspect of the invention relates to a Gov$^a$ specific antibody. The antibody that recognizes specifically a Gov$^a$ allele-specific CD109 epitope corresponding to the polypeptide encoded by a CD109 nucleic acid optionally contains an A at the position corresponding to position 2108 of SEQ ID NO:1 and position 954 of SEQ ID NO:5, and containing the amino acid Tyrosine at the position corresponding to position 703 of the CD109 protein encoded by SEQ ID NO:1. Another aspect of the invention relates to a Gov$^b$ specific antibody. The antibody that recognizes specifically a Gov$^b$ allele-specific CD109 epitope corresponding to the polypeptide encoded by a CD109 nucleic acid optionally contains a C at the position corresponding to position 2108 of SEQ ID NO:3 and position 954 of SEQ ID NO:5, and containing the amino acid Serine at the position corresponding to position 703 of the CD109 protein encoded by SEQ ID NO:3. The antibody is typically a monoclonal antibody or a polyclonal antibody and further comprises a detectable label. Another aspect of the invention relates to an immunogenic composition comprising a Gov specific antibody. The method of Gov alloantigen phenotyping a subject, optionally comprises:
(a) providing a CD109 polypeptide sample derived from the subject; and
(b) detecting the presence of a Gov$^a$ or a Gov$^b$ antigen in the CD109 polypeptide.

The CD109 is typically membrane bound CD109 or isolated CD109. The detection step optionally comprises contacting the polypeptide sample with an antibody described herein. A diagnostic kit for Gov alloantigen phenotyping a subject, optionally comprises a Gov$^a$ antibody and/or a Gov$^b$ antibody of the invention. The kit optionally further comprises a container.

The invention also includes an isolated polypeptide containing a Gov$^a$ allele-specific amino acid sequence and which is specifically reactive with a Gov$^a$ antibody. The invention also includes an isolated polypeptide containing Gov$^b$ allele-specific amino acid sequence and which is specifically reactive with a Gov$^b$ antibody. The isolated polypeptide optionally comprises between 4 and 100 amino acids. The isolated polypeptide also optionally comprises a full-length CD109 polypeptide, or a fragment of a CD109 polypeptide. The invention also includes an isolated CD109 polypeptide fragment, comprising a Gov$^a$ or a Gov$^b$ antigen.

The polypeptide fragment optionally comprises all of, or a fragment of, the protein encoded by SEQ ID NO:1, and in which the amino acid corresponding to position 703 of the protein encoded by SEQ ID NO:1 is a Tyrosine. The polypeptide fragment optionally comprises all of, or a fragment of, the protein encoded by SEQ ID NO:3, and in which the amino acid corresponding to position 703 of the protein encoded by SEQ ID NO:3 is a Serine. The polypeptide fragment optionally comprises between 4 and 100 amino acids. The polypeptide fragment optionally comprises between 7 and 50 amino acids. The polypeptide is optionally purified from native CD109, or is synthetic, or is prepared by recombinant means. The polypeptide fragment is optionally bound to a substrate. The invention also includes a fusion compound comprising the polypeptide of the invention connected to an immunogenic carrier. The fusion compound typically includes an immunogenic carrier comprising a proteinaceous carrier. The immunogenic carrier optionally comprises a detectable label. The invention also includes a Gov$^a$ or Gov$^b$ specific antibody recognizing the fusion compound. The invention also includes an immunogenic composition comprising the polypeptide, polypeptide fragment or fusion compound. Another aspect of the invention relates to a method of producing a Gov$^a$ or Gov$^b$ specific antibody, comprising contacting an animal with the immunogenic composition so that the animal produces antibodies against the immunogenic composition. The animal is typically a bird or a mammal.

The invention also includes a method of screening an antibody producing culture to determine whether the culture produces Gov$^a$ or Gov$^b$ specific antibody, comprising:
(a) contacting a polypeptide of the invention with the culture; and
(b) detecting Gov$^a$ or Gov$^b$ specific antibody.

The polypeptide typically comprises a detectable label. The polypeptide is optionally attached to a substrate. The invention also includes a method of purifying a Gov allele-specific antibody from a sample, comprising:
(a) contacting a Gov allele-specific antibody with a polypeptide of the invention comprising a Gov$^a$ or Gov$^b$ antigen, so that an antibody:polypeptide complex is formed;
(b) separating the complex from the sample; and
(c) next separating the antibody from the polypeptide.

The polypeptide is optionally bound to a substrate. The polypeptide optionally comprises a detectable label. Another aspect of the invention relates to a method of purifying a Gov polypeptide from a sample, comprising:
(a) contacting a Gov allele-specific antibody with a polypeptide of the invention containing a Gov$^a$ or Gov$^b$-specific epitope, so that an antibody:polypeptide complex is formed;
(b) separating the complex from the sample; and
(c) next separating the antibody from the polypeptide.

The antibody is optionally bound to a substrate. The antibody optionally comprises a detectable label.

The invention also includes a method of screening a subject sample to determine whether the sample contains Gov$^a$ or Gov$^b$-specific antibodies, comprising:
(a) contacting a polypeptide of the invention with the sample; and
(b) detecting the presence or absence of Gov$^a$ or Gov$^b$ specific antibody.

The polypeptide optionally comprises a detectable label. The polypeptide is optionally attached to a substrate. The subject optionally comprises a mother of a fetus or a newborn infant, or the fetus or newborn infant itself, and the presence of $Gov^a$ or $Gov^b$-specific antibody indicates that the fetus or infant has, or is at risk of NAIT. In such a case, the presence of $Gov^a$ or $Gov^b$ specific antibody indicates that the subject has, or is at risk of a blood disease, disorder or abnormal physical state, for example, that comprises bleeding of the subject, or increased risk of bleeding, due to destruction of blood platelets. The blood disease, disorder or abnormal physical state typically comprises post-transfusion purpura ("PTP"), post-transfusion platelet refractoriness ("PR") or neonatal alloimmune thrombocytopenia (NAIT). The sample optionally comprises human serum or plasma. Another aspect of the invention relates to a diagnostic kit for detection of $Gov^a$ or $Gov^b$ specific antibody, comprising a polypeptide described herein. The kit optionally further comprises a container.

Another aspect of the invention relates to a method of determining Gov antibody specificity, comprising:
(a) contacting an antibody with a first polypeptide comprising a $Gov^a$ antigen and a second polypeptide comprising a $Gov^b$ antigen; and
(b) determining whether the antibody binds to either or both of the first and second polypeptide.

Another aspect involves a method of blocking $Gov^a$ antibody binding to an antigen, comprising: contacting the antibody with a polypeptide of the invention comprising a $Gov^a$ antigen so that an antibody:polypeptide complex is formed. The polypeptide optionally comprises a detectable label. The polypeptide is optionally bound to a substrate. The invention also includes a pharmaceutical composition comprising the polypeptide. Another aspect of the invention relates to a method of immunizing a subject so that the subject will produce anti-idiotypic antibodies, comprising administering to the subject the immunogenic composition.

The invention also includes a method of blocking $Gov^a$ or $Gov^b$ specific antibodies from binding to CD109 in a subject, comprising: administering to the subject polypeptides of the invention capable of binding to $Gov^a$ and/or $Gov^b$ specific antibodies. The subject has or is at risk of a blood disease, disorder or abnormal physical state. The polypeptide optionally comprises a detectable label. The binding of the polypeptide to the $Gov^a$ or $Gov^b$ specific antibody prevents alloimmune cell destruction by the antibody. The binding of the polypeptide to the $Gov^a$ or $Gov^b$-specific antibody depletes the antibody. The blood disease, disorder or abnormal physical state typically comprises bleeding of the subject, or increased risk of bleeding, due to alloimmune destruction of blood platelets, such as post-transfusion purpura ("PTP"), post-transfusion platelet refractoriness ("PR") or neonatal alloimmune thrombocytopenia ("NAIT").

DETAILED DESCRIPTION OF THE INVENTION

Definitions

The following definitions are provided in order to aid those skilled in the art in understanding the detailed description of the present invention.

The term "alloantigens" refers to antigens of an individual that are responsible for eliciting an alloimmune response.

The phrase "alloimmune response" refers to an immune response, which occurs when antibodies from one individual react against antigens of a different individual of the same species.

The phrase "anti-idiotypic antibodies" refers to antibodies which can bind endogenous or foreign idiotypic antibodies and which can be used to treat or prevent pathological conditions associated with an immune response to a foreign alloantigen.

The phrase "$Gov^a$/$Gov^b$ biallelic system" refers to a system of human platelet alloantigens in which an individual can be homozygous for either $Gov^a$ or $Gov^b$ allelic forms of CD109, or an individual can be $Gov^a$/$Gov^b$ heterozygous for CD109.

"GPI" refers to glycosylphosphatidylinositol.

The term "NATP" refers to neonatal alloimmune thrombocytopenia.

"Nucleic acid" includes DNA and RNA, whether single or double stranded. The term is also intended to include a strand that is a mixture of nucleic acids and nucleic acid analogs and/or nucleotide analogs, or that is made entirely of nucleic acid analogs and/or nucleotide analogs.

"Nucleic acid analogue" refers to modified nucleic acids or species unrelated to nucleic acids that are capable of providing selective binding to nucleic acids or other nucleic acid analogues. As used herein, the term "nucleotide analogues" includes nucleic acids where the internucleotide phosphodiester bond of DNA or RNA is modified to enhance biostability of the oligomer and "tune" the selectivity/specificity for target molecules (Ulhmann, et al., 1990, Angew. Chem. Int. Ed. Eng., 90: 543; Goodchild, 1990, J. Bioconjugate Chem., I: 165; Englisch et al., 1991, Angew, Chem. Int. Ed. Eng., 30: 613). Such modifications may include and are not limited to phosphorothioates, phosphorodithioates, phosphotriesters, phosphoramidates or methylphosphonates. The 2'-O-methyl, allyl and 2'-deoxy-2'-fluoro RNA analogs, when incorporated into an oligomer show increased biostability and stabilization of the RNA/DNA duplex (Lesnik et al., 1993, Biochemistry, 32: 7832). As used herein, the term "nucleic acid analogues" also include alpha anomers (α-DNA), L-DNA (mirror image DNA), 2'-5' linked RNA, branched DNA/RNA or chimeras of natural DNA or RNA and the above-modified nucleic acids. For the purposes of the present invention, any nucleic acid containing a "nucleotide analogue" shall be considered as a nucleic acid analogue. Backbone replaced nucleic acid analogues can also be adapted to for use as immobilised selective moieties of the present invention. For purposes of the present invention, the peptide nucleic acids (PNAs) (Nielsen et al, 1993, Anti-Cancer Drug Design, 8: 53; Engels et al., 1992, Angew, Chem. Int. Ed. Eng., 31: 1008) and carbamate-bridged morpholino-type oligonucleotide analogs (Burger, D. R., 1993, J. Clinical Immunoassay, 16: 224; Uhlmann, et al., 1993, Methods in Molecular Biology, 20, "Protocols for Oligonucleotides and Analogs," ed. Sudhir Agarwal, Humana Press, NJ, U.S.A., pp. 335-389) are also embraced by the term "nucleic acid analogues". Both exhibit sequence-specific binding to DNA with the resulting duplexes being more thermally stable than the natural DNA/DNA duplex. Other backbone-replaced nucleic acids are well known to those skilled in the art and may also be used in the present invention (See e.g., Uhlmann et al 1993, Methods in Molecular Biology, 20, "Protocols for Oligonucleotides and Analogs," ed. Sudhir Agrawal, Humana Press, NJ, U.S.A., pp. 335).

The term "PTP" refers to post-transfusion purpura.

The term "PTPR" refers to post-transfusion platelet refractorines.

"SNP" refers to single nucleotide polymorphism.

The standard, one-letter codes "A," "C," "G," and "T" are used herein for the nucleotides adenylate, cytidylate, guanylate, and thymidylate, respectively. The skilled will understand that, in DNAs, the nucleotides are 2'-deoxyribonucleotide-5'-phosphates (or, at the 5'-end, possibly triphosphates)

while, in RNAs, the nucleotides are ribonucleotide-5'-phosphates (or, at the 5'-end, possibly triphosphates) and uridylate (U) occurs in place of T. "N" means any one of the four nucleotides. On occasion herein, dA, dC, dG and dT might be used for the respective 2'-deoxyribonucleotides.

Unless otherwise specified or required by the context, "nucleic acid" means DNA or RNA and "nucleotide" means ribonucleotide or 2'-deoxyribonucleotide.

Reference herein to a "full-length" CD109 molecule or protein means the 1445-amino acid-long polypeptide, for which the amino acid sequence, deduced from a cDNA sequence, is provided in SEQ ID NO:1 and in SEQ ID NO:3 and which is denoted as the full-length translated product (i.e., including the amino-terminal leader peptide, and excluding carboxyl-terminal processing associated with GPI anchor addition). The Gov$^a$ alloantigen bearing form of CD109 may be referred to herein as $^{703}$Tyr CD109. The Gov$^b$ alloantigen bearing form of CD109 may be referred to herein as $^{703}$Ser CD109.

It has been determined that a single nucleotide of the CD109 gene is responsible for the Gov polymorphism in CD109. Extensive serological studies initially demonstrated that the polymorphism underlying the Gov system resides solely on the CD109 molecule [Sutherland, D. R. (1991); Smith et al. (1995)]. Further, extensive deglycosylation of CD109 does not affect the binding the anti-Gov$^a$ and anti-Gov$^b$ antibodies to molecules of the appropriate phenotype, or to cells bearing the appropriate CD109 variant, indicating that carbohydrate residues are not involved in the formation of Gov antigenic epitopes. Further work has indicated that the Gov allele-specific antibody binding can however, be abrogated by denaturation of CD109 with the detergent SDS [Smith et al. (1995)]. Taken together, these observations indicate that the Gov alleles of CD109 are protein epitopes that are likely defined by the primary amino acid sequence of CD109.

Following the isolation of a CD109 cDNA the nature of the two Gov alleles was characterised further using platelet RNA-derived cDNA in the polymerase chain reaction ("PCR"). Platelet mRNA transcripts were obtained from serologically defined Gov$^{a/a}$, Gov$^{a/b}$ and Gov$^{b/b}$ individuals. The RNA was then converted to cDNA, and the entire CD109 cDNA coding region was then amplified as a series of overlapping PCR products. The Gov$^a$ [SEQ ID NO:1] and Gov$^b$ [SEQ ID NO:3] alleles differ by an A to C substitution at position 2108 of the coding region of the CD109 cDNA. This single nucleotide polymorphism also results in a BstNI restriction site in the Gov$^b$ allele that is not present in its Gov$^a$ counterpart. On the basis of this BstNI site, Gov$^a$ can by distinguished from Gov$^b$ by restriction fragment length polymorphism (RFLP) analysis. This single nucleotide polymorphism can also be detected by SSCP analysis, and by allele-specific hybridization studies, including "Real-Time" PCR analyses.

As a result of this $A^{2108}C$ single nucleotide polymorphism, the Gov$^a$ allele [SEQ ID NO:2] of CD109 contains a Tyr at position 703 of the full-length protein, while the Gov$^b$ allele [SEQ ID NO:4] contains a Ser in this position. The polymorphism does not alter the ability of Gov$^a$ and Gov$^b$ homozygous platelets to adhere to collagen types I, III and V. Additionally, the binding of anti-Gov$^a$ and anti-Gov$^b$ antibodies to platelets of the appropriate phenotype did not interfere with platelet adhesion to any of the above collagen types. Thus, while the Tyr$^{703}$Ser results in the formation of the Gov alloantigen epitopes, it does not appear to impair platelet function.

Identification and characterisation of the Gov alloantigen system permits pre- and post-natal diagnosis of the Gov phenotype of an individual, providing a warning for the possibility of NATP, PTP and PTPR. Allelic Gov typing of CD109 equates with the Gov status of the CD109 protein of an individual. The Gov system led to diagnostic and therapeutic strategies to avoid or control diseases that result from Gov incompatibility. The present invention can be applied to these tasks and goals in a variety of ways, illustrative examples of which are discussed below.

For example, an oligonucleotide probe can be synthesized, in accordance with the present invention, that will hybridize to a cDNA segment, derived from CD109 mRNA, that contains the nucleotide G at polymorphic nucleotide 2108 (nucleotide=guanylate). Alternatively, an oligonucleotide probe can be synthesized that will hybridize with a CD109 cDNA segment containing the base adenine at nucleotide 2108 (nucleotide=adenylate). These allele-specific probes can be appropriately labelled and added to the generated cDNA segments under annealing conditions, such that only one of the allele-specific probes hybridizes and can be detected, thereby identifying the specific Gov$^a$ or Gov$^b$ allele. In accordance with conventional procedures, the design of an oligonucleotide probe according to the present invention preferably involves adjusting probe length to accommodate hybridization conditions (temperature, ionic strength, exposure time) while assuring allele-specificity. A length of ten to thirty nucleotides is typical.

Diagnostic kits can also be used, in accordance with the present invention, for the determination and diagnosis of alloantigen phenotypes via the procedures described herein. Such a kit can include, among others, antibodies or antibody fragments to an antigenic determinant expressed by either of the above-described Gov$^a$- and Gov$^b$-encoding sequences. These antibodies would react with the blood sample of an individual so as to indicate whether that individual has a Gov$^a$ or Gov$^b$ phenotype. Alternatively, all the reagents required for the detection of nucleotide(s) that distinguish the Gov alloantigens, by means described herein, can be provided in a single kit that uses isolated genomic DNA, platelet (or other cellular) mRNA or total RNA, or corresponding cDNA from an individual. A kit containing a labelled probe that distinguishes, for example, nucleotide 2108 of CD109 can be utilised for Gov alloantigen genotyping and phenotyping.

A further beneficial use of the nucleotide sequences that distinguish the Gov$^a$ allele from the Gov$^b$ allele is to obtain or synthesize the respective expression product, in the form of a peptide or polypeptide, encoded by these nucleotide sequences. These polypeptides can be used to generate antibodies for diagnostic and therapeutic uses, for example, with regard to pathological conditions such as PTP, PTPR or NATP. These polypeptides can also be used diagnostically to detect the presence of Gov$^a$ or Gov$^b$ specific antibodies in patient plasma or serum, or used therapeutically (see below; assays may be adopted, for example, from U.S. Pat. No. 5,851,788).

A polypeptide within the present invention which can be used for the purpose of generating such antibodies preferably comprises an amino-acid sequence that corresponds to (i.e., is coincident with or functionally equivalent to) a fragment of the CD109 molecule that includes amino acid 703. When amino acid 703 is Tyrosine, the polypeptide can be used, as described above, to produce antibodies that specifically bind the Gov$^a$ form of CD109; in contrast, when it is Serine, antibodies can be obtained that specifically recognise the Gov$^b$ form. The class of polypeptides thus defined, in accordance with the present invention, is not intended to include the native CD109 molecule, but does encompass fragments of the molecule, as well as synthetic polypeptides meeting the aforementioned definition.

Although the length of a polypeptide within this class is not critical, the requirement for immunogenicity may require that the polypeptide be attached to an immunogenicity-imparting carrier. Such carriers include a particulate carrier such as a liposome or a soluble macromolecule (protein or polysaccharide) with a molecular weight in the range of about 10,000 to 1,000,000 Daltons Additionally, it may be desirable to administer the polypeptide with an adjuvant, such as complete Freund's adjuvant. For artificial polypeptides, as distinguished from CD109 fragments, maximum length is determined largely by the limits of techniques available for peptide synthesis, which are currently about fifty amino acids. Thus, a synthetic polypeptide of the present invention is preferably between four to about fifty amino acids in length.

In the context of the present invention, the term "antibody" encompasses monoclonal and polyclonal antibodies produced by any available means. Such antibodies can belong to any antibody class (IgG, IgM, IgA, etc.) and may be chimeric. Examples of the preparation and uses of polyclonal antibodies are disclosed in U.S. Pat. Nos. 5,512,282, 4,828,985, 5,225,331 and 5,124,147 which are incorporated by reference in their entirety. The term "antibody" also encompasses antibody fragments, such as Fab and F(ab')$_2$ fragments, of anti-Gov$^a$ or anti-Gov$^b$ antibodies, conjugates of such fragments, and so-called "antigen binding proteins" (single-chain antibodies) which are based on anti-Gov$^a$ or anti-Gov$^b$ antibodies, in accordance, for example, with U.S. Pat. No. 4,704,692, the contents of which are hereby incorporated by reference. Alternatively, monoclonal antibodies or fragments thereof within the present invention can be produced using conventional procedures via the expression of isolated DNA that encodes variable regions of such a monoclonal antibody in host cells such as *E. coli* (see, e.g., Ward et al., Nature, 341:544-546 (1989)) or transfected murine myeloma cells (see Gillies et al., Biotechnol. 7:799-804 (1989); Nakatani et al., Biotechnol. 7:805-810 (1989)). For additional examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705 that are incorporated by reference in their entirety.

While human alloantisera currently used for serological typing are specifically excluded from this definition, the use of CD109 or Gov allele-specific peptides to detect anti-Gov antibodies in human plasma or serum, or to determine the specificity of such alloantibodies, are specifically included. Similarly, the use of such CD109 peptides or Gov allele-specific peptides to purify CD109 antibodies, or allele-specific CD109 antibodies from human serum is specifically included. Similarly, the use in vitro of such CD109 peptides or Gov allele-specific peptides to deplete allele-specific antibody activity from human serum samples, or to block CD109 antibody binding, or allele-specific antibody binding, is specifically included.

Diagnostic applications of these antibodies are exemplified, according to the present invention, by the use of a kit containing an anti-Gov$^a$ or an anti-Gov$^b$ antibody, which undergoes a reaction with a sample of an individual's blood to determine a Gov$^a$ or Gov$^b$ platelet phenotype. Such a reaction involves the binding of anti-Gov$^a$ antibody to Gov$^a$ antigen or the binding of anti-Gov$^b$ antibody to Gov$^b$ antigen. The observation of antibody-antigen complex in a blood sample would indicate a positive result. A kit of this type could be used to diagnose, or to help prevent the occurrence of pathological conditions like PTP, PTPR, or NATP.

A polypeptide of the present invention that is recognised specifically by anti-Gov$^a$ or anti-Gov$^b$ antibodies can also be used therapeutically. Thus, antibodies raised against such a polypeptide can be employed in the generation, via conventional methods, of anti-idiotypic antibodies, that is, antibodies that bind an anti-Gov$^a$ or anti-Gov$^b$ antibody. See, e.g., U.S. Pat. No. 4,699,880, the contents of which are hereby incorporated by reference. Such anti-idiotypic antibodies would bind endogenous or foreign anti-Gov antibodies in the blood of an individual, which would treat or prevent pathological conditions associated with an immune response to a "foreign" Gov alloantigen. Alternatively, a polypeptide within the present invention can be administered to an individual, with a physiologically-compatible carrier, to achieve the same qualitative effect, namely, the selective reduction or elimination of circulating anti-Gov antibodies from a patient suffering or at risk from an immune response, or the abrogation by competitive binding to administered peptide, of the binding of Gov-specific antibodies to the platelets of such an individual The present invention is further described below by reference to the following, illustrative examples.

Example 1

PCR Amplification and Analysis of PCR Products

Platelet total RNA was isolated from EDTA anticoagulated blood of Gov$^{aa}$ and Gov$^{bb}$ individuals in the manner described in Lymann et al., Blood 75:2343-48 (1990). First, platelet mRNA in 10 µl aliquots was heated to 70° C. for 10 minutes and quickly cooled on ice before reverse transcription. The first strand cDNA was then synthesized using 10 µM oligo dT, 40 units RNAsin (Promega), 2 mM of each dNTP (dN triphosphate) (Pharmacia), 500 units of cloned MMLV reverse transcriptase and 5× enzyme buffer (Gibco) in a total volume of 50 µl. The cDNA synthesis was carried out at 42° C. for 45 minutes and was stopped by chilling to 0° C.

Overlapping sets of oligonucleotide primers (Table 2) based on the sequence of CD109 were then used to amplify by PCR the entire coding region of platelet CD109 in 8 overlapping segments that spanned the entire CD109 open reading frame.

TABLE 2

| Fragment | Sense Primer | | Antisense Primer | Size (bp) | Annealing Temperature (° C.) |
|---|---|---|---|---|---|
| 1 | K1-80<br>5' GTAGCCCAGGCAGACGCC 3'<br>(SEQ ID NO: 15) | (−24) | K1-650<br>5' GTGACAACCACTGTTGGATCAA 3'<br>(SEQ ID NO: 23) | 544 | 568 59 |

TABLE 2-continued

| Fragment | Sense Primer | | Antisense Primer | Size (bp) | Annealing Temperature (° C.) |
|---|---|---|---|---|---|
| 2 | K1-1<br>5' CGCATTGTTACACTCTTCTC 3'<br>(SEQ ID NO: 16) | 445 | K1-1120<br>5' TACATTTCTTGAAATACCTG 3'<br>(SEQ ID NO: 24) | 1014 570 | 50 |
| 3 | K1-1022<br>5' GATTCTTCAAATGGACTTT 3'<br>(SEQ ID NO: 17) | 910 | K1-REV-1<br>5' GGCTGTGTCACAGAGATC 3'<br>(SEQ ID NO: 25) | 1747 838 | 50 |
| 4 | K1-1400<br>5' TGAATTCCCAATCCTGGAGGA 3'<br>(SEQ ID NO: 18) | 1291 | GSP3<br>5' GCCACCCAAGAAGTGATAGA 3'<br>(SEQ ID NO: 26) | 2165 875 | 55 |
| 5 | K1-M43<br>5' TTCAGGAATGTGGACTCTGG 3'<br>(SEQ ID NO: 19) | 1898 | 6R4N<br>5' CGGCTTCAAGGAAACATCT 3'<br>(SEQ ID NO: 27) | 2998 1101 | 56 |
| 6 | K1-3080<br>5' CTGGGAGCACTTGGTTGTCA 3'<br>(SEQ ID NO: 20) | 2948 | 1-5N<br>5' CAGCAACATCTAAATCAAAGGC 3'<br>(SEQ ID NO: 28) | 3859 912 | 56 |
| 7 | K1-3570<br>5' ACAATTTCAGACTTCTGAGG 3'<br>(SEQ ID NO: 21) | 3462 | 7U3N<br>5' CACAGCCAAAGTTCCATA 3'<br>(SEQ ID NO: 29) | 4337 876 | 50 |
| 8 | K1-3920<br>5' GACGAAGATCTATCCAAAATC 3'<br>(SEQ ID NO: 22) | 3812 | K1-4600<br>5' GCTAGGACCTGTTGTACACC 3'<br>(SEQ ID NO: 30) | 4489 678 | 55 |

Table 2 lists the position of the 5' end of each oligonucleotide with respect to the CD109 cDNA sequence, which includes both 3' and 5' untranslated regions, is noted in parentheses. The CD109 ORF encompasses nucleotides 1-4335 of the published CD109 cDNA, and corresponds exactly to the CD109 cDNA sequence presented in SEQ ID NO:1. The size of each PCR product, and the annealing temperature used for the corresponding primer pair, is listed.

PCR reactions (50:1) containing 1×PCR buffer (Gibco Life Technologies), 1.5 mM MgCl$_2$, 200:M of each dNTP, 1:M of each primer, 1.25 units Taq polymerase (Gibco Life Technologies), and 3:1 cDNA underwent 40 cycles of 94° C. (45 seconds), primer-specific annealing temperature (Table 2; 45 seconds), and 72° C. (45-60 seconds), using a Perkin Elmer 2400 thermocycler. PCR products (30:1) were subsequently size-separated electrophoretically on a 1.2% agarose/TAE gel containing 1:g/ml ethidium bromide. Bands were subsequently excised and purified (50:1) using the QIAquick (Qiagen) kit for direct sequencing and subcloning. Sequencing reactions (3-5:I purified product per reaction) were carried out using the Thermosequenase Cy5.5 dye terminator sequencing kit (Amersham Pharmacia Biotech) and the same primers that had been used for initial PCR amplification (Table 2), or selected internal CD109-specific primers as appropriate, and were subsequently analysed using the Open Gene automated DNA sequencing system (Visible Genetics). In parallel, PCR products were cloned into Pmel-digested pMAB1, a pBS SK(−) (Stratagene) derivative containing a Pmel restriction site within the polylinker. Resultant plasmid clones were analysed by alkaline lysis/restriction digestion, and as appropriate (and following an additional overnight 13% PEG/1.6 M NaCl precipitation), by DNA sequence analysis as above. By combining direct PCR sequencing and the analysis of subcloned fragments, it was ensured that the DNA sequence of each PCR-derived cDNA fragment was obtained independently at least twice, with each fragment being sequenced in both directions in its entirety.

This analysis revealed that the CD109 cDNA sequences of Gov$^{aa}$ and Gov$^{bb}$ individuals differed by a single nucleotide at position 2108 of the sequence shown in SEQ ID NO:1. Gov$^{a/a}$ individuals have an A at position 2108, whereas Gov$^{b/b}$ individuals have a C at the same position. This change results in a Tyr-Ser amino acid polymorphism at residue 703 of the full-length CD109 polypeptide chain. This single nucleotide polymorphism also results in a BstNI restriction site in the Govb allele that is not present in the Gov$^a$ allele. Analysis of the other regions of the CD109 cDNA in their entirety revealed no other nucleotide differences that segregated with Gov phenotype (i.e., that could be used to distinguish the Gov$^a$ allele from the Gov$^b$ allele).

To facilitate subsequent genomic DNA analyses of the Gov$^{a/b}$ alleles, the intron/exon junctions of the exon bearing the putative Gov-specific nucleotide substitution identified above, as well as the DNA sequence of the flanking introns, were determined. CD109 cDNA-specific oligonucleotides binding in the vicinity of this substitution were used for the direct sequencing of p4L10, a pCYPAC_1-derived PAC clone bearing the human CD109 locus using the Open Gene system (Visible Genetics) as above. The nucleotide sequence of the Gov polymorphism-containing exon, as well as of the flanking introns, is presented in SEQ ID NO:5. The Gov polymorphism lies at nucleotide position 954 in SEQ ID NO:5. Subsequent work has mapped the intron-exon structure of the entire human CD109 locus, and has determined that the Gov single nucleotide polymorphism of CD109 lies in exon 19 of the CD109 gene.

Example 2

RFLP Analysis of PCR Amplified Genomic DNA

The A-C Gov CD109 polymorphism corresponds to the internal nucleotide of the first complete codon of exon 19 of the CD109 gene. As this exon comprises only 118 nucleotides, and the Gov polymorphism lies almost at the extreme 5' end of this exon, we determined the nucleotide sequence of both introns flanking this exon to facilitate subsequent genomic DNA analyses of the Gov$^{a/b}$ alleles. The DNA sequence of CD109 exon 19 and its flanking introns (CD109 introns 18 and 19) is presented as SEQ ID NO:5. To confirm that the A to C polymorphism at position 2108 of the CD109 open reading frame (nucleotide 2108, SEQ ID NO: 1; nucleotide 954, SEQ ID NO:5) segregates with the Gov phenotype, RFLP analysis was carried out on PCR amplified genomic CD109 DNA using the BstNI restriction endonuclease, which recognises the DNA sequence 5' CCAGG 3' found in the Gov$^b$ cDNA (nucleotides position 2108-2112 in SEQ ID NO:3; the corresponding Gov$^a$ sequence, 5' ACAGG 3', is nucleotides 2108-2112 in SEQ ID NO:1). This enzyme does not cleave at 5' ACAGG 3' (found in Gov$^a$; nucleotides 2108-2112 in SEQ ID NO: 1). A 448 bp genomic fragment was PCR-amplified from Gov$^{aa}$, Gov$^{ab}$, and Gov$^{bb}$ individuals using the pair of oligonucleotides SEQ ID NO:9 and SEQ ID NO:10. These oligonucleotides flank exon 19. The former binds within intron 18 (nucleotides 875-892 SEQ ID NO:5), while the latter binds within intron 19 to the sequence complementary to nucleotides 1305-1322 of SEQ ID NO:5). The resultant 448 bp PCR product, when digested with BstNI, yielded the restriction fragments predicted on the basis that the A to C polymorphism at position 2108 (SEQ ID NO: 1) segregates with the Gov phenotype.

Example 3

Hybridization Analysis of PCR Amplified Genomic DNA

To further confirm that the A to C polymorphism at position 2108 of the CD109 open reading frame (nucleotide 2108, SEQ ID NO:1; nucleotide 954, SEQ ID NO:5) segregates with the Gov phenotype, we also performed an alternative analysis involving the selective hybridization of Gov allele-specific DNA probes to PCR amplified genomic CD109 DNA. Two primers flanking the polymorphic A-C site at position 2108 (SEQ ID NO:1; position 954, SEQ ID NO:5) were designed to amplify by PCR a 105 bp genomic DNA fragment containing the polymorphic site from genomic DNA isolated from Gov$^{aa}$, Gov$^{ab}$, and Gov$^{bb}$ individuals. The first primer (SEQ ID NO:11) binds within intron 18 to nucleotides 902-928 of SEQ ID NO:5. The second primer (SEQ ID NO:12) binds within exon 19 to the sequence complementary to nucleotides 977-1106 of SEQ ID NO:5. Two additional nucleotide probes were designed—one specific for the target sequence of the Gov$^a$ allele of the CD109 gene, and the other for the Gov$^b$ allele of the CD109 gene. The first probe (SEQ ID NO:13) overlaps the CD109 intron 18/exon 19 junction, binds to the Gov$^a$ allele at nucleotides 935-974 of SEQ ID NO:5, and was tagged with the fluorescent dye 6-FAM. The second probe (SEQ ID NO:14), also overlapping the CD109 intron 18/exon 19 junction, binds to the Gov$^b$ allele at the position corresponding to nucleotides 935-971 of SEQ ID NO:5, and was tagged with the fluorescent dye VIC. Genomic DNA was isolated from Gov phenotyped human peripheral blood leukocytes, and PCR/hybridization analysis was carried out using Taqman real-time PCR technology (Perkin Elmer). Genomic DNA was amplified using primers SEQ ID NO:11 and SEQ ID NO:12, with each reaction additionally containing 100 nM FAM-labelled Gov$^a$ probe and 200 nM VIC-labelled Gov$^b$ probe. Allelic discrimination, based on allele-specific fluorescence, was then determined using a post-PCR plate reader (Perkin Elmer). In all cases, PCR/fluorescence-based Gov genotyping correlated with the Gov phenotype, indicating that the A to C polymorphism at position 2108 (SEQ ID NO: 1) does indeed segregate with the Gov phenotype.

Example 4

SSP Analysis of PCR Amplified Genomic DNA

To further confirm that the A to C polymorphism at position 2108 of the CD109 open reading frame (nucleotide 2108, SEQ ID NO:1; nucleotide 954, SEQ ID NO:5) segregates with the Gov phenotype, we also performed an alternative analysis involving SSCP analysis of PCR amplified genomic CD109 DNA. Two Gov allele-specific antisense oligonucleotides—SEQ ID NO:6 and SEQ ID NO:7—differing by a single 3' nucleotide (and binding to sequence complementary to nucleotides 954-976 of SEQ ID NO:5, and of the Gov$^b$ counterpart of SEQ ID NO:5, respectively), were combined with a common sense primer—SEQ ID NO:8 binds within intron 18 and which corresponds to nucleotides 752-773 of SEQ ID NO:5, to amplify a 225 bp genomic DNA fragment containing the Gov polymorphic site from genomic DNA isolated from Gov$^{aa}$, Gov$^{ab}$, and Gov$^{bb}$ individuals. In all cases, complete concordance between PCR-SSP analysis and Gov phenotyping was observed.

SEQUENCES

SEQ ID NO: 1 consists of the entire 4335 nucleotide CD109 cDNA open reading frame encoding the Gov$^a$ allele. The Gov$^a$ allele comprises an A at nucleotide position 2108.

SEQ ID NO:2 consists of the entire 1445 aa protein sequence produced from CD109 Gov$^a$ cDNA. The Gov$^a$ allele comprises a Tyr at amino acid 703.

SEQ ID NO: 3 consists of the entire 4335 nucleotide CD109 cDNA open reading frame encoding the Gov$^b$ allele. The Gov$^b$ allele comprises a C at nucleotide position 2108.

SEQ ID NO: 4 consists of the entire 1445 aa protein sequence produced from the CD109 Gov$^b$ cDNA. The Gov$^b$ allele comprises a Ser at amino acid 703.

SEQ ID NO: 5 consists of the CD109 genomic DNA comprising CD109 exon 19 and the flanking introns, introns 18 and 19. The 118 nucleotide exon 19, comprising nucleotides 952-1069 of SEQ ID NO:5, corresponds to nucleotides 2106-2223 of SEQ ID NO: 1. The A to C Gov polymorphism of CD109 (corresponding to nucleotide 2108 of SEQ ID NO: 1) therefore corresponds to nucleotide 954 of SEQ ID NO:5. In the Gov$^a$ allele, nucleotide 954 is A, while in the Gov$^b$ allele nucleotide 954 is C. Thus, SEQ ID NO:5 corresponds to the Gov$^a$ allele of CD109. Within SEQ ID NO:5, nucleotides 1-951 correspond to CD109 intron 18, while nucleotides 1070-2608 correspond to intron 19.

We note that nucleotides 2108-2112 of SEQ ID NO: 1, and the corresponding nucleotides 954-958 of SEQ ID NO:5, which consist of the sequence 5' ACAGG 3' (and which contains the Gov$^a$ allele-specific polymorphic nucleotide at its 5' end), is not cleavable by the restriction endonuclease BstNI. However, in the corresponding Gov$^b$ allele, the corresponding sequence—5' CCAGG 3'—is cleavable by BstNI, and that the two Gov alleles can be discriminated on this basis. We note also that a group of restriction endonucleases—Bst2UI, BstNI, BstOI, EcoRII, MaeIII, MspR91, MvaI, or ScrFI (or one of their isoschizomers)—is capable of differentiating between the Gov$^a$ and Gov$^b$ alleles on this basis.

SEQ ID NO:6-SEQ ID NO:14 comprise oligonucleotides for the PCR amplification of Gov polymorphism containing CD109 sequence from RNA, cDNA derived from RNA, or from genomic DNA, and for the Gov typing analyses of such amplified DNA fragments.
SEQ ID NO:6.
SEQ ID NO: 3, an antisense oligonucleotide specific for the Gov$^a$ allele, binds to exon 19 sequence complementary to nucleotides 954-976 of SEQ ID NO:5. SEQ ID NO:6 and SEQ ID NO: 7 (see below) differ by a single allele-specific 3' nucleotide
SEQ ID NO:7.
SEQ ID NO:7, an antisense oligonucleotide specific for the Gov$^b$ allele, binds to exon 19 sequence complementary to nucleotides 954-976 of the Gov$^b$ counterpart of SEQ ID NO:5. SEQ ID NO:6 (see above) and SEQ ID NO:7 differ by a single allele-specific 3' nucleotide.
SEQ ID NO:8.
SEQ ID NO:8 binds within intron 18, and corresponds to nucleotides 752-773 of SEQ ID NO:5.
SEQ ID NO:9.
SEQ ID NO:9 binds within intron 18 (nucleotides 875-892 SEQ ID NO:5).
SEQ ID NO:10.
SEQ ID NO:10 binds within intron 19 to the sequence complementary to nucleotides 1305-1322 of SEQ ID NO:5.
SEQ ID NO:11
SEQ ID NO:11 binds within intron 18 to nucleotides 902-928 of SEQ ID NO:5.
SEQ ID NO:12.
SEQ ID NO:12, binds within exon 19 to the sequence complementary to nucleotides 977-1006 of SEQ ID NO:5.
SEQ ID NO:13.
SEQ ID NO:13, specific for the Gov$^a$ allele, overlaps the CD109 intron 18/exon 19 junction, and binds to the Gov$^a$ allele at nucleotides 935-974 of SEQ ID NO:5.
SEQ ID NO:14.
SEQ ID NO:14, specific for the Gov$^b$ allele, overlaps the CD109 intron 18/exon 19 junction, and binds to the Gov$^b$ allele at the position corresponding to nucleotides 935-971 of SEQ ID NO:5.

We claim:

1. An isolated monoclonal antibody that binds a $Gov^a$ allele-specific CD109 epitope but does not bind a $Gov^b$ allele-specific CD109 epitope.

2. The antibody of claim 1, that recognizes specifically a $Gov^a$ allele-specific CD109 epitope corresponding to the polypeptide encoded by a CD109 nucleic acid containing an A at the position corresponding to position 2108 of SEQ ID NO:1 and position 954 of SEQ ID NO:5, and containing the amino acid Tyrosine at the position corresponding to position 703 of the CD109 protein encoded by SEQ ID NO:1.

3. An isolated monoclonal antibody that binds a $Gov^b$ allele-specific CD109 epitope but does not bind a $Gov^a$ allele-specific CD109 epitope.

4. The antibody of claim 3, that recognizes specifically a $Gov^b$ allele-specific CD109 epitope corresponding to the polypeptide encoded by a CD109 nucleic acid containing a C at the position corresponding to position 2108 of SEQ ID NO:3 and position 954 of SEQ ID NO:5, and containing the amino acid Serine at the position corresponding to position 703 of the CD109 protein encoded by SEQ ID NO:3.

5. The antibody of claim 1, further comprising a detectable label.

6. An immunogenic composition comprising an isolated Gov$^a$ allele-specific CD109 peptide capable of generating the antibody of claim 1.

7. A diagnostic kit for Gov alloantigen phenotyping a subject, comprising a Gov$^a$ antibody of claim 1.

8. The kit of claim 7, further comprising a container.

9. The antibody of claim 3, further comprising a detectable label.

10. An immunogenic composition comprising an isolated Gov$^b$ specific-allele CD109 peptide capable of generating the antibody of claim 3.

11. A diagnostic kit for Gov alloantigen phenotyping a subject, comprising a Gov$^b$ antibody of claim 3.

12. The kit of claim 11, further comprising a container.

* * * * *